US007071172B2

(12) United States Patent
McCown et al.

(10) Patent No.: US 7,071,172 B2
(45) Date of Patent: Jul. 4, 2006

(54) SECRETION SIGNAL VECTORS

(75) Inventors: Thomas J. McCown, Carrboro, NC (US); Rebecca P. Haberman, Hillsborough, NC (US)

(73) Assignee: The University of North Carolina at Chapel Hill, Chapel Hill, NC (US)

(*) Notice: Subject to any disclaimer, the term of this patent is extended or adjusted under 35 U.S.C. 154(b) by 0 days.

(21) Appl. No.: 10/425,328

(22) Filed: Apr. 29, 2003

(65) Prior Publication Data
US 2003/0228284 A1   Dec. 11, 2003

Related U.S. Application Data

(60) Provisional application No. 60/376,628, filed on Apr. 30, 2002.

(51) Int. Cl.
*A61K 31/70* (2006.01)
*A61K 39/23* (2006.01)
*C07H 21/04* (2006.01)
*C12N 15/86* (2006.01)

(52) U.S. Cl. .................. 514/44; 424/233.1; 536/23.1; 536/23.2; 536/23.5; 536/23.51; 536/24.1; 435/320.1; 435/455; 435/456

(58) Field of Classification Search ............. 435/320.1; 536/23.4, 23.5; 434/93.2
See application file for complete search history.

(56) References Cited

U.S. PATENT DOCUMENTS

| 5,342,762 | A | * | 8/1994 | Mosher et al. ............. 435/69.1 |
| 5,618,677 | A | * | 4/1997 | Ni et al. ..................... 435/7.1 |
| 6,040,172 | A |  | 3/2000 | Kaplitt |
| 6,180,613 | B1 |  | 1/2001 | Kaplitt et al. |
| 6,365,394 | B1 | * | 4/2002 | Gao et al. .................... 435/239 |

FOREIGN PATENT DOCUMENTS

WO   WO 92/15015   *   9/1992

OTHER PUBLICATIONS

Watson (Nucl. Acids Res. 12(13): 5145-5164).*
Patel et al (EMBO 6:2565-2572, 1987).*
Yurchenko et al (J. Biol. Chem. 268(11): 8356-8365, 1993).*
Schwarzbauer (J. Cell. Biol. 113(6): 1463-1473, 1991).*
GenBank Accession No. NM_002026 (Nov. 15, 2001).*
GenBank Accession No. Q91740 (Jul. 15, 1999).*
DeSimone et al (Dev. Biol. 149 (2), 357-369 (1992).*
Samulski et al (J. Virol. 63(9): 3822-3828, 1989).*
D'Ercole et al (Progress in Growth Factor Research 6(2-4): 1995), abstract only.*
During et al., "Glucagon-like peptide-1 receptor is involved in learning and neuroprotection," Abstract, *Nat. Med.* (Aug. 17, 2003).

Freese et al., "Direct Gene Transfer Into Human Epileptogenic Hippocampal Tissue with an Adeno-Associated Virus Vector: Implications for a Gene Therapy Approach to Epilepsy," *Epilepsia* 38(7): 759-766 (1997).
Goss et al., "Herpes Simplex-Mediated Gene Transfer of Nerve Growth Factor Protects Against Peripheral Neuropathy in Streptozotocin-Induced Diabetes in the Mouse," *Diabetes* 51 2227-2232 (Jul. 2002).
Haberman et al., "Inducible long-term gene expression in brain with adeno-associated virus gene transfer," *Gene Therapy* 1604-1611 (1998).
Haberman et al., "Therapeutic Liabilities of *in Vivo* Viral Vector Tropism: Adeno-Associated Virus Vectors, NMDAR1 Antisense, and Focal Seizure Sensitivity," *Molecular Therapy* 6(4) 495-500.
Haberman, et al., "Regulated Suppression of Focal Seizure Sensitivity by Adeno-Associated Virus (AAV) Vector-Dependent Galanin Secretion," Program No. 619.10 *Abstract Viewer/Itinerary Planner* Washington, DC: Society for Neuroscience (2002).
Huber et al., "Grafts of adenosine-releasing cells suppress seizures in kindling epilepsy," *PNAS* 98(13) 7611-7616 (2001).
Kaplitt et al., "Long-term gene expression and phenotypic correction using adeno-associated virus vectors in the mammalian brain," *Nature Genetics* 8 148-154 (1994).
Klein et al., "NGF gene transfer to intrinsic basal forebrain neurons increases cholinergic cell size and protects from age-related, spatial memory deficits in middle-aged rats," *Elsevier Science B.V., Brain Research* 875 144-151 (2000).
Kordower et al., "Neurodegeneration Prevented by Lentiviral Vecotr Delivery of GDNF in Primate Models of Parkinson's Disease," *Science* 290 767-772 (Oct. 27, 2000).

(Continued)

*Primary Examiner*—Richard Schnizer
(74) *Attorney, Agent, or Firm*—Myers, Bigel, Sibley & Sajovec, P.A.

(57) ABSTRACT

The present invention provides delivery vectors for transferring a nucleic acid sequence to a cell in vitro, ex vivo or in vivo. The delivery vector comprises a segment encoding a secretory signal peptide. In embodiments of the invention, the delivery vector is an adeno-associated virus (AAV) vector. In other embodiments, the secretory signal peptide is a fibronectin secretory signal peptide (including variations and modifications, thereof). The delivery vectors of the invention may further comprise a heterologous nucleic acid sequence encoding a polypeptide of interest for transfer to a target cell, where the polypeptide of interest is operably associated with the secretory signal. Also disclosed are methods of transferring a nucleic acid of interest to a cell using the delivery vectors of the invention.

16 Claims, 5 Drawing Sheets

OTHER PUBLICATIONS

Larsson et al., "Suppression of Insult-Induced Neurogenesis in Adult rat Brain by Brain-Derived Neurotrophic Factor," *Experimental Neurology* 177 1-8 (2002).

Luo et al., "Subthalamic GAD Gene Therapy in a Parkinson's Disease Rat Model," *Science* 298 425-429 (Oct. 11, 2002).

Manno et al., "AAV-mediated actor IX gene transfer to skeletal muscle in patients with severe hemophilia B," *Blood* 101(8) 2963-2972 (Apr. 15, 2003).

McCown et al., "Differential and persistent expression patterns of CNS gene transfer by a adeno-associated virus (AAV) vector," *Elsvier Science B.V., Brain Research* 99-107 (1996).

Naldini et al., "Efficient transfer, integration, and sustained long-term expression of the transgene in adult rat brains injected with a lentiviral vector," *Proc. Natl. Acad. Sc.I. USA* 93 11382-11388 (Oct. 1996).

Xia et al., "the HIV Tat protein transduction domain improves the biodistribution of β-glucuronidase expressed form recombinant viral vectors," *Nature Biotechnology* 19 640-644 (Jul. 2001).

* cited by examiner

AAV Fibronectin signal sequence constructs

AAV-GFP
 3.4 kb

AAV-FIB-GFP
 3.5 kb

AAV-FIB- GAL
 2.9 kb

AAV-FIB-NPY
 2.9 kb

AAV-FIBtTAk
 3.9kb

AAV-FIB-GAL/tTAk
 3.3kb

AAV-FIB-NPY/tTAk
 3.3kb

SEQUENCE LISTING

```
<160> NUMBER OF SEQ ID NOS: 23

<210> SEQ ID NO 1
<211> LENGTH: 96
<212> TYPE: DNA
<213> ORGANISM: Rattus norvegicus
<220> FEATURE:
<221> NAME/KEY: CDS
<222> LOCATION: (1)..(96)
<223> OTHER INFORMATION: Rat fibronectin secretory signal coding
      sequence

<400> SEQUENCE: 1 atg ctc agg ggt ccg gga ccc ggg cgg ctg ctg ctg cta gca gtc ctg     48
Met Leu Arg Gly Pro Gly Pro Gly Arg Leu Leu Leu Leu Ala Val Leu
1               5                   10                  15 tgc ctg ggg aca tcg gtg cgc tgc acc gaa acc ggg aag agc aag agg     96
Cys Leu Gly Thr Ser Val Arg Cys Thr Glu Thr Gly Lys Ser Lys Arg
            20                  25                  30

<210> SEQ ID NO 2
<211> LENGTH: 32
<212> TYPE: PRT
<213> ORGANISM: Rattus norvegicus

<400> SEQUENCE: 2

Met Leu Arg Gly Pro Gly Pro Gly Arg Leu Leu Leu Leu Ala Val Leu
1               5                   10                  15

Cys Leu Gly Thr Ser Val Arg Cys Thr Glu Thr Gly Lys Ser Lys Arg
            20                  25                  30

<210> SEQ ID NO 3
<211> LENGTH: 114
<212> TYPE: DNA
<213> ORGANISM: Rattus norvegicus
<220> FEATURE:
<221> NAME/KEY: CDS
<222> LOCATION: (1)..(114)
<223> OTHER INFORMATION: Rat fibronectin secretory signal coding
      sequence and coding sequences 3' of cleavage site
<220> FEATURE:
<221> NAME/KEY: misc_feature
<222> LOCATION: (96)..(97)
<223> OTHER INFORMATION: Secretory signal cleavage site
<220> FEATURE:
<221> NAME/KEY: misc_feature
<222> LOCATION: (97)..(114)
<223> OTHER INFORMATION: Rat fibronectin coding sequences 3' of cleavage
      site

<400> SEQUENCE: 3
```

```
atg ctc agg ggt ccg gga ccc ggg cgg ctg ctg ctg cta gca gtc ctg      48
Met Leu Arg Gly Pro Gly Pro Gly Arg Leu Leu Leu Leu Ala Val Leu
1               5                   10                  15 tgc ctg ggg aca tcg gtg cgc tgc acc gaa acc ggg aag agc aag agg      96
Cys Leu Gly Thr Ser Val Arg Cys Thr Glu Thr Gly Lys Ser Lys Arg
            20                  25                  30 cag gct cag caa atc gtg                                             114
Gln Ala Gln Gln Ile Val
        35

<210> SEQ ID NO 4
<211> LENGTH: 38
<212> TYPE: PRT
<213> ORGANISM: Rattus norvegicus

<400> SEQUENCE: 4

Met Leu Arg Gly Pro Gly Pro Gly Arg Leu Leu Leu Leu Ala Val Leu
1               5                   10                  15

Cys Leu Gly Thr Ser Val Arg Cys Thr Glu Thr Gly Lys Ser Lys Arg
            20                  25                  30

Gln Ala Gln Gln Ile Val
        35

<210> SEQ ID NO 5
<211> LENGTH: 26
<212> TYPE: PRT
<213> ORGANISM: Homo sapiens

<400> SEQUENCE: 5

Met Leu Arg Gly Pro Gly Pro Gly Leu Leu Leu Leu Ala Val Gln Cys
1               5                   10                  15

Leu Gly Thr Ala Val Pro Ser Thr Gly Ala
            20                  25

<210> SEQ ID NO 6
<211> LENGTH: 31
<212> TYPE: PRT
<213> ORGANISM: Xenopus laevis

<400> SEQUENCE: 6

Met Arg Arg Gly Ala Leu Thr Gly Leu Leu Leu Val Leu Cys Leu Ser
1               5                   10                  15

Val Val Leu Arg Ala Ala Pro Ser Ala Thr Ser Lys Lys Arg Arg
            20                  25                  30

<210> SEQ ID NO 7
<211> LENGTH: 101
<212> TYPE: DNA
<213> ORGANISM: Artificial sequence
<220> FEATURE:
<223> OTHER INFORMATION: Synthetic oligonucleotide

<400> SEQUENCE: 7
ccggtatgct caggggtccg ggacccgggc ggctgctgct gctagcagtc ctgtgcctgg     60
ggacatcggt gcgctgcacc gaaaccggga agagcaagag g                        101

<210> SEQ ID NO 8
<211> LENGTH: 101
<212> TYPE: DNA
<213> ORGANISM: Artificial sequence
<220> FEATURE:
<223> OTHER INFORMATION: Synthetic oligonucleotide
```

-continued

<400> SEQUENCE: 8
ccggcctctt gctcttcccg gtttcggtgc agcgcaccga tgtccccagg cacaggactg        60
ctagcagcag cagccgcccg ggtcccggac ccctgagcat a                          101

<210> SEQ ID NO 9
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 9
ccggtaatgg gctggaccct gaac                                             24

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
taatgggctg gaccctgaac                                                  20

<210> SEQ ID NO 11
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 11
gctcatgtga ggccatgctt g                                                21

<210> SEQ ID NO 12
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 12
ggccgctcat gtgaggccat gcttg                                            25

<210> SEQ ID NO 13
<211> LENGTH: 74
<212> TYPE: DNA
<213> ORGANISM: Rattus norvegicus
<220> FEATURE:
<221> NAME/KEY: misc_feature
<222> LOCATION: (18)..(74)
<223> OTHER INFORMATION: Transferrin secretory signal coding sequence

<400> SEQUENCE: 13
ccacacacac cgagaggatg aggttcgctg tgggtgccct gctggcttgt gccgccctgg        60
gactgtgtct ggct                                                        74

<210> SEQ ID NO 14
<211> LENGTH: 78
<212> TYPE: DNA
<213> ORGANISM: Homo sapiens
<220> FEATURE:
<221> NAME/KEY: misc_feature
<222> LOCATION: (1)..(78)

-continued

<223> OTHER INFORMATION: Human fibronectin 1 secretory signal coding
      sequence

<400> SEQUENCE: 14
atgcttaggg gtccggggcc cgggctgctg ctgctggccg tccagtgcct ggggacagcg    60
gtgccctcca cgggagcc                                                  78

<210> SEQ ID NO 15
<211> LENGTH: 93
<212> TYPE: DNA
<213> ORGANISM: Xenopus laevis
<220> FEATURE:
<221> NAME/KEY: misc_feature
<222> LOCATION: (1)..(93)
<223> OTHER INFORMATION: Fibronectin secretory signal coding sequence

<400> SEQUENCE: 15
atgcgccggg gggccctgac cgggctgctc ctggtcctgt gcctgagtgt tgtgctacgt    60
gcagccccct ctgcaacaag caagaagcgc agg                                 93

<210> SEQ ID NO 16
<211> LENGTH: 11
<212> TYPE: PRT
<213> ORGANISM: Artificial sequence
<220> FEATURE:
<223> OTHER INFORMATION: Canonical secretory signal sequence

<400> SEQUENCE: 16

Leu Leu Leu Leu Ala Val Leu Cys Leu Gly Thr
1               5                   10

<210> SEQ ID NO 17
<211> LENGTH: 19
<212> TYPE: PRT
<213> ORGANISM: Rattus norvegicus

<400> SEQUENCE: 17

Met Arg Phe Ala Val Gly Ala Leu Leu Ala Cys Ala Ala Leu Gly Leu
1               5                   10                  15

Cys Leu Ala

<210> SEQ ID NO 18
<211> LENGTH: 79
<212> TYPE: DNA
<213> ORGANISM: Artificial sequence
<220> FEATURE:
<223> OTHER INFORMATION: Synthetic oligonucleotide

<400> SEQUENCE: 18
ccggtccaca cacaccgaga ggatgaggtt cgctgtgggt gccctgctgg cttgtgccgc    60
cctgggactg tgtctggct                                                 79

<210> SEQ ID NO 19
<211> LENGTH: 79
<212> TYPE: DNA
<213> ORGANISM: Artificial sequence
<220> FEATURE:
<223> OTHER INFORMATION: Synthetic oligonucleotide

<400> SEQUENCE: 19
ccggagccag acacagtccc agggcggcac aagccagcag gcacccaca gcgaacctca     60 tcctctcggt gtgtgtgga                                                 79

```
<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
tgctagcagt cctgtgcctg                                              20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
atgtgaggcc atgcttgtcg                                              20

<210> SEQ ID NO 22
<211> LENGTH: 17
<212> TYPE: PRT
<213> ORGANISM: Rattus norvegicus
<220> FEATURE:
<221> NAME/KEY: MISC_FEATURE
<222> LOCATION: (1)..(17)
<223> OTHER INFORMATION: Preprocathepsin L secretory signal sequence

<400> SEQUENCE: 22

Met Thr Pro Leu Leu Leu Leu Ala Val Leu Cys Leu Gly Thr Ala Leu
1               5                   10                  15

Ala

<210> SEQ ID NO 23
<211> LENGTH: 22
<212> TYPE: PRT
<213> ORGANISM: Homo sapiens
<220> FEATURE:
<221> NAME/KEY: MISC_FEATURE
<222> LOCATION: (1)..(22)
<223> OTHER INFORMATION: Prepro-alpha 2 type collagen secretory signal
      sequence

<400> SEQUENCE: 23

Met Leu Ser Phe Val Asp Thr Arg Thr Leu Leu Leu Leu Ala Val Thr
1               5                   10                  15

Leu Cys Leu Ala Thr Cys
            20
```

SECRETION SIGNAL VECTORS

RELATED APPLICATION INFORMATION

This application claims the benefit of U.S. Provisional Application No. 60/376,628; filed Apr. 30, 2002, which is incorporated by reference herein in its entirety.

STATEMENT OF FEDERAL SUPPORT

This invention was made, in part, with government support under grant number NS35633 from the National Institutes of Health. The United States government has certain rights to this invention.

FIELD OF THE INVENTION

The present invention relates to delivery vectors; more particularly, the present invention concerns delivery vectors for transferring a nucleic acid sequence of interest to a cell of the central nervous system.

BACKGROUND OF THE INVENTION

Epilepsies comprise a remarkably diverse collection of disorders that affect 1–4% of the population in the United States alone. Current therapy is symptomatic. Available drugs reduce seizure frequency in the majority of patients, but it is estimated that only about forty percent are free of seizures despite optimal treatment. From a clinical point of view three types of epilepsy have been defined: (1) petit mal, which is characterized by the absence of seizures or small seizures, (2) grand mal, which comprise generalized catatonic seizures, and (3) complex partial, which is often localized in temporal lobe seizures. The third form is the most common, and it is often resistant to medical treatment. Surgical resection is often the only form of treatment that eliminates seizures in the majority of these resistant patients.

Recombinant adeno-associated virus (rAAV) vectors are useful for gene therapy to the central nervous system (CNS) because these vectors have been found to be non-toxic and have been demonstrated to provide long-term gene expression in the brain (McCown et al., (1996) *Brain Res.* 713:99) and endogenous gene expression can be controlled using a tetracycline-off, regulatable element (Haberman et al., (1998) *Gene Ther.* 5:1604).

Focal seizure disorders present an attractive gene therapy target, especially when considering viral vectors as the method of gene delivery. Within the focus, neurons are the cells ultimately responsible for seizure activity, so the ability of viral vectors, such as adeno-associated virus (AAV) and lentivirus, to stably transduce neurons provides access to cells that directly mediate seizure activity (Kaplitt et al., (1994) *Nature Genet.* 8:148; McCown et al., 1996) *Brain Res.* 713:99; Naldini et al., (1996) *Proc. Nat. Acad. Sci.* 93:11382). In addition, there appear to be a number of gene therapy targets that modulate neuronal excitability, such as neurotransmitter receptors and ion channels. In order to pursue these targets, one must consider the opponent nature of inhibitory and excitatory processes in the brain. For example, when the N-methyl-D-aspartic acid (NMDA) excitatory amino acid receptor was targeted with an AAV delivered antisense, focal seizure sensitivity was significantly reduced (Haberman et al., (2002) *Mol. Ther.* 6:495). However, merely replacing the cytomegalovirus (CMV) promoter with a tetracycline regulated promoter caused the opposite effect, an increase in focal seizure sensitivity. That the two promoters transduced different populations of neurons with only slight overlap suggested an explanation for these seemly contradictory findings. In one case inhibitory interneurons likely comprised the majority of transduced cells, while in the other instance primary excitatory output neurons comprised the preponderance of transduced cells. Therefore, when targeting neurotransmitter receptors or ion channels, the pattern of neuronal tropism can be crucial to the actual physiological outcome.

The adeno-associated viruses (AAV) are members of the family *Parvoviridae* and the genera *Dependoviruses*. Serotypes 1 through 4 were originally identified as contaminates of adenovirus preparations (Carter and Laughlin (1984) in, *The Parvoviruses* p. 67–152 New York, N.Y.) whereas type 5 was isolated from a patient wart that was HPV positive. To date, seven molecular clones have been generated representing the serotypes of AAV (Bantel-Schaal et al. (1999) *J. Virol.* 73: 939, Chiorini et al. (1999) *J. Virol.* 73:1309, Muramatsu et al. (1996) *Virology* 221:208, Rutledge et al. (1998) *J. Virol.* 72:309, Srivastava et al. (1983) *J. Virol.* 45:555, Xiao et al. (1999) *J. Virol.* 73:3994). These clones have provided valuable reagents for studying the molecular biology of serotype specific infection. Transduction of these viruses naturally results in latent infections, with completion of the life cycle generally requiring helper functions not associated with AAV viral gene products. As a result, all of these serotypes are classified as non-pathogenic and believed to share a safety profile similar to the more extensively studied AAV type 2 (Carter and Laughlin (1984) in, *The Parvoviruses* p. 67–152 New York, N.Y.).

The extensive development of AAV type 2 as a vector has been facilitated by 30 years of studying its biology in vitro. Recombinant AAV type 2 (rAAV2) has proven to be a suitable gene transfer vector in many different organisms (Monohan and Samulski (2000) *Gene Ther.* 7:24, Rabinowitz and Samulski (1998) *Curr. Opin. Biotechnol.* 9:470). As the number of applications evaluating gene transfer increases in vitro and in vivo, limitations to efficient rAAV type 2 transduction have become apparent (Bartlett et al. (2000) *J. Virol.* 74:2777, Davidson et al. (2000) *Proc. Natl. Acad. Sci. USA* 97:3428, Hansen et al. (2001) *J. Virol.* 75:4080, Samulski et al. (1999) in, Adeno-associated viral vectors Cold Spring Harbor, N.Y., Walters et al. (2000) *J. Virol* 74:535, Xiao et al. (1999) *J. Virol.* 73:3994, Zabner et al. (2000) *J. Virol.* 74:3852). The natural tropism of any virus, including rAAV type 2, is a fundamental limitation to efficient gene transfer. With the identification of the AAV type 2 receptor, the requirements for efficient entry in target cells have become an active topic of study (Summerford and Samulski (1998) *J. Virol.* 72:1438). Efforts have been made to overcome these restrictions by broadening the host range using either bispecific antibodies to the virion shell (Bartlett et al. (1999) *Nat. Biotechnol.* 17:181) or through capsid insertional mutagenesis (international patent publication WO 00/28004; Rabinowitz et al. (1999) *Virology* 265:274; Girod et al. (1999) *Nat. Med.* 5:1052, Wu et al. (2000) *J.Virol.* 74:8635). While these efforts are beginning to bare fruit, utilizing the other serotypes of AAV may yet provide additional resources for making safe and efficient gene transfer vectors. To this end, a number of studies have begun to show the utility of serotype specific vectors in vitro and in vivo (International patent publication WO 00/28004; Chao et al. (2000) *Mol. Ther.* 2:619, Chao et al., (2001) *Mol. Ther.* 4:217, Chiorini et al. (3999) *J. Virol.* 73:1309, Chiorini et al. (1998) *Mol. Cell. Biol.* 18:5921, Davidson et al. (2000) *Proc. Natl. Acad. Sci. USA* 97:3428, Hildinger et al. (2001) *J. Virol.* 75:6199, Xiao et al. (1999) *J. Virol.* 783:3994, Zabner et al. (2000) *J. Virol.* 74:3852). In general, each of these studies uncovered broader cell type specificity with increased gene transfer in vivo.

U.S. Pat. No. 6,180,613 describes a method of delivering exogenous DNA to a target cell within the mammalian CNS using a rAAV vector. Haberman et al., (1998) *Gene Ther.* 5:1604, disclose a dual cassette rAAV vector comprising a reporter gene under the control of a tetracycline-responsive system and the tetracycline transactivator. However, these systems are constrained by the fact that the gene product influences only the cell that has been transduced.

There is an ongoing need in the art for improved methods of nucleic acid delivery to the central nervous system.

SUMMARY OF THE INVENTION

The present invention addresses the problems of differential promoter tropism and the opponent nature of inhibition and excitory process in the CNS discussed above by producing the polypeptide of interest in a form that is secreted from the target cell. In this way, the desired endpoint (e.g., modulation of seizures) can be achieved independently of the particular cell types that take up the delivery vector and produce the polypeptide of interest. To date, gene therapy approaches have focused primarily upon producing a gene product within the transduced cell, such that any secretion would inevitably depend upon cellular processes specific to the gene product. Unfortunately, most of these processes are tightly regulated, and in the case of synaptic release, the site of action can be quite distal to the site of gene expression. According to the present invention, the secretory process does not typically depend upon cellular activity or utilize a specialized vesicular release mechanism, such as stimulus dependent neurotransmitter release, to attain effective polypeptide secretion following delivery.

The results of the investigations disclosed herein are markedly different from those in a previous study on constitutive gene product secretion and seizures. Huber et al., (2001) *Proc. Nat. Acad. Sci.* 98:7611) reported that in vivo secretion of adenosine from genetically modified fibroblasts attenuated limbic kindled seizures. Although substantial seizure suppression was obtained during the first week post-ventricular cell grafting, by the fourth week post-graft, the suppression was totally gone. This loss of antiseizure efficacy was attributed to the decline in viable, grafted cells over this period. In contrast, the present studies show that with a secreted protein, seizure attenuation can be achieved over a long period of time. For example, the regulation studies in the inferior colliculus described herein demonstrate the ability to significantly attenuate seizure activity ten weeks after infusion of a delivery vector. Furthermore, since the area of viral transduction in these studies was relatively localized (McCown et al., (1996) *Brain Res.* 713:99), the gene product was secreted in close proximity to the area of seizure genesis, not throughout the entire brain. This property should minimize potential deleterious side effects inherent to the global distribution of neuroactive substances in the brain.

As one aspect, the present invention provides delivery vectors for transferring a nucleic acid to a cell, the delivery vector comprising a segment encoding a secretory signal peptide. In embodiments of the invention, the delivery vector is a viral vector. In other representative embodiments, the delivery vector is an adeno-associated virus (AAV) vector. In still other embodiments, the secretory signal peptide is a fibronectin secretory signal peptide.

The delivery vectors of the invention may further comprise a heterologous chimeric nucleic acid sequence encoding a polypeptide of interest for transfer to a target cell, where the polypeptide of interest is operably associated with the secretory signal peptide.

In other representative embodiments, the present invention provides a delivery vector comprising a heterologous chimeric nucleic acid sequence comprising (i) a segment encoding a polypeptide of interest, and (ii) a segment encoding a fibronectin secretory signal peptide that is operatively associated therewith, said heterologous chimeric nucleic acid sequence encoding a fusion polypeptide. In particular embodiments, the delivery vector is a viral delivery vector.

The invention further provides a recombinant AAV (rAAV) vector genome comprising a heterologous chimeric nucleic acid sequence comprising (i) a segment encoding a polypeptide of interest, and (ii) a segment encoding a fibronectin secretory signal peptide that is operatively associated therewith, said heterologous chimeric nucleic acid sequence encoding a fusion polypeptide.

In other embodiments, the invention provides a viral particle comprising a recombinant viral vector genome comprising the heterologous chimeric nucleic acid sequence described above. In illustrative embodiments, the recombinant viral vector genome is a rAAV vector genome comprising 5' and 3' inverted terminal repeat (ITR) sequences.

The methods of the invention may be used to deliver a nucleic acid sequence to a cell in vitro, ex vivo, or in vivo for a variety of purposes, including but not limited to, protein production, generation of animal models, diagnostics, gene discovery and characterization, and therapy. In particular embodiments, the invention is practiced to deliver a nucleic acid sequence to a cell of the central nervous system (CNS).

The present invention may be used to produce a secreted polypeptide, e.g., for polypeptide production, to deliver a polypeptide to cells surrounding the area of transduction, or to deliver the polypeptide to the systemic circulation or lymph. In addition, the methods of the invention allow for expression of a transgene independently of the normal cellular stimuli. For example, in the case of the CNS, neuropeptides are typically produced in response to cell generated stimuli such as electrical signaling or other endogenous signals. The secretory signal sequences of the invention will target the associated polypeptide to the secretory pathway in the cell and will remove expression from the control of endogenous signals. In this manner, greater control of neuropeptide expression may be achieved in the CNS.

The present invention further provides for the use of a delivery vector of the invention for the manufacture of a medicament for the delivery of a nucleic acid sequence to a cell in vitro, ex vivo, or in vivo.

The foregoing and other objects and aspects of the present invention are explained in detail in the specification set forth below.

DETAILED DESCRIPTION OF PREFERRED EMBODIMENTS

Figure 1:
FIG. 1—The structure of recombinant AAV fibronectin signal sequence containing plasmid constructs.
Figure 1:
Figure 1:
Figure 1:
Figure 1:
Figure 1:
Figure 1:

The present invention provides a method of gene delivery whereby secretion of polypeptides from cells (e.g., in the central nervous system) is enhanced by the addition of a suitable secretory signal sequence (e.g., derived from fibronectin). The present invention may facilitate a wide variety of applications in which it is desirable for the gene product to influence cells surrounding an area of transduction, the gene product must be secreted to reach its target, to achieve systemic delivery of the gene product, and/or to attain improved regulation of expression and secretion of the gene product.

In particular embodiments, the present invention provides a means to secrete neuroactive peptides from a gene delivery vector (e.g., a viral vector) in a less restrictive manner than the normal secretion patterns of neuropeptides. This non-restricted secretion pattern may allow the peptides to be secreted from any transduced cell, and to more effectively alter neuronal properties such as seizure sensitivity.

In other particular embodiments, the present invention provides a method of attenuating focal seizure genesis. As part of the investigations described herein, a rAAV vector has been developed wherein the coding sequence for specific polypeptides is preceded by the secretion signal sequence for the laminar protein, fibronectin. In a number of in vitro studies, it is demonstrated that the inclusion of this fibronectin secretory sequence leads to the secretion of the gene product from the transduced cell. When the coding sequence for the neuroactive peptide, galanin, was placed into this rAAV vector, transduction of the inferior colliculus resulted in a significant elevation of the seizure initiation threshold over a prolonged period. Subsequently, reduction in endogenous gene expression by oral administration of doxycycline caused a return of the seizure threshold to baseline levels. Clearly, expression of galanin significantly suppressed seizure sensitivity in the inferior colliculus. In addition, the fibronectin signal sequence-galanin fusion protein was able to protect hippocampal neurons from kainic acid seizure-induced cell death. These characteristics are not shared by all secretory signal peptides, as the secretory signal from transferrin did not produce secretion of a reporter gene in vitro as was found for the fibronectin signal sequence.

Further, the coding sequence for rat neuropeptide Y (NPY) has been placed into this rAAV vector, and following infusion of the recombinant virus into the inferior colliculus, a significant elevation of the collicular seizure threshold has been observed over a period of several months. Together, these results suggest that functional NPY gene product is being secreted in the area of transduction, and the effect of this secretion is the suppression of seizure sensitivity. This effect may be relatively persistent given the long-term gene expression that can be obtained with this rAAV vector (Haberman et al., 1998) and the relative lack of tolerance to the seizure suppressive actions of NPY (Klemp and Woldbye, (2001) *Peptides* 22:523). Accordingly, the present invention provides a non-toxic tool to administer neuropeptide Y (NPY) endogenously over a long time period to inhibit seizure sensitivity.

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR §1.822 and established usage. See, e.g., *Patentin User Manual*, 99–102 (November 1990) (U.S. Patent and Trademark Office).

Except as otherwise indicated, standard methods known to those skilled in the art may be used for the construction of recombinant virus, parvovirus and rAAV constructs, cloning genes, amplifying and detecting nucleic acids, and the like. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

I. Definitions

The following terms are used in the description herein and the appended claims:

The term "secretory signal activity" as used herein is intended to indicate a signal peptide that functions to target a polypeptide operatively associated therewith (e.g., by covalent peptide bonds to form a fusion polypeptide) to the cellular secretory pathway. It is not necessary that the signal peptide directs all of the polypeptide to the secretory pathway. Secretory signal peptides according to the invention are discussed in more detail hereinbelow.

The term "vector" or "delivery vector" as used herein is intended broadly and encompasses both viral and non-viral transfer vectors as known in the art, including single-stranded and double-stranded nucleic acid vectors as well as DNA, RNA, and DNA/RNA chimeric vectors. Exemplary viral vectors include, but are not limited to, adenovirus, herpesvirus, lentivirus, parvovirus (e.g., AAV), baculovirus and Epstein Barr Virus vectors. Illustrative non-viral vectors include, but are not limited to, plasmid, phage, yeast artificial chromosomes (YACs), Bacterial Artificial Chromosomes (BACs), and naked DNA vectors (e.g., by liposomal delivery), or synthetic nucleotide vectors (e.g., vectors that are generated by PCR methods or oligonucleotide synthesis, as known in the art). In particular embodiments, a parvovirus or AAV delivery vector is used. Delivery vectors are described in more detail below.

With respect to viral gene delivery systems, the term "vector" or "delivery vector" may refer to a virus particle (e.g., AAV) that functions as a gene transfer vehicle, and which comprises a recombinant viral DNA or RNA (i.e., the vector genome) packaged within a virion (e.g., AAV viral DNA [vDNA] within an AAV capsid). Alternatively, in some contexts, the term "vector" may be used to refer to the recombinant vector genome alone, which need not be delivered in the form of a viral particle.

A "heterologous" nucleic acid or "heterologous" nucleic acid sequence will typically be a sequence that is not naturally occurring in the delivery vector (e.g., virus delivery vector). Alternatively, a heterologous nucleic acid sequence may refer to a viral sequence that is placed into a non-naturally occurring environment (e.g., by association with a promoter or coding sequence with which it is not naturally associated in the virus).

As used herein, a "recombinant" delivery vector comprises a heterologous nucleic acid to deliver to a target cell. A "recombinant virus vector genome", a "recombinant parvovirus vector genome" or a "recombinant AAV vector genome" is a virus, parvovirus or AAV genome (i.e., vDNA), respectively, into which a heterologous (e.g., foreign) nucleotide sequence has been inserted. A "recombinant virus particle", "recombinant parvovirus particle" or "recombinant AAV particle" comprises a recombinant virus, parvovirus or AAV vector genome, respectively, packaged within a viral, parvovirus or AAV virion, respectively.

The term "tropism" as used herein refers to entry of the virus into the cell, optionally followed by expression (e.g., transcription and, optionally, translation) of sequences carried by the viral genome in the cell, e.g., for a recombinant virus, expression of the heterologous nucleotide sequences(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of AAV, gene expression from the viral genome may be from a stably integrated provirus, from a non-integrated episome, as well as any other form in which the virus may take within the cell.

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide), but may further be a single or double stranded sequence.

A "chimeric nucleic acid" comprises two or more nucleic acid sequences covalently linked together to encode a fusion polypeptide. The nucleic acids may be DNA, RNA, or a hybrid thereof.

Likewise, a "fusion polypeptide" comprises two or more polypeptides covalently linked together, typically by peptide bonding.

As used herein, an "isolated" polynucleotide (e.g., an "isolated DNA" or an "isolated RNA") means a polynucleotide separated or substantially free from at least some of the other components of the naturally occurring organism or virus, for example, the cell or viral structural components or other polypeptides or nucleic acids commonly found associated with the polynucleotide.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

A "therapeutic polypeptide" is a polypeptide that may alleviate or reduce symptoms that result from an absence or defect in a polypeptide in a cell or subject. Alternatively, a "therapeutic polypeptide" is one that otherwise confers a benefit to a subject, e.g., controls or decreases the likelihood of onset of a condition or disease state or provides some amelioration of an existing disease state or slows the progression thereof.

"An immunogenic polypeptide" is a polypeptide that induces an active immune response in a subject, e.g., for vaccination against a pathogenic organism or cancer.

By the terms "treat," "treating" and "treatment" with respect to a particular condition or disease state, it is intended that the severity of the condition or disease state is reduced and/or some beneficial effect is provided to the subject. Alternatively, the terms "treat," "treating" or "treatment" may indicate that administration of the inventive delivery vectors slows, controls, or decreases the likelihood or probability, or delays the onset of, the condition or disease state in the subject.

A "therapeutically effective" amount as used herein is an amount that provides sufficient expression of the heterologous nucleotide sequence delivered by the vector to provide some improvement or benefit to the subject. Alternatively stated, a "therapeutically effective" amount is an amount that will provide some alleviation, mitigation, or decrease in at least one clinical symptom in the subject or that will delay, control or decrease the likelihood of onset of a condition or disease state in the subject. Those skilled in the art will appreciate that the therapeutic effects need not be complete or curative, as long as some benefit is provided to the subject.

The term "about", as used herein when referring to a measurable value such as an amount of virus (e.g., titer), dose (e.g., an amount of a non-viral vector), time, temperature, and the like, is meant to encompass variations of ±20%, ±10%, ±5%, ±1%, ±0.5%, or even ±0.1% of the specified amount.

II. Secretion Signal Delivery Vectors.

The delivery vectors of the invention may be any vector known in the art, including single-stranded and double-stranded vectors and including DNA, RNA, and DNA/RNA chimeric vectors. The vector may be a viral or non-viral vector. Exemplary viral vectors include, but are not limited to, adenovirus, herpesvirus, lentivirus, AAV, baculovirus and Epstein Barr Virus vectors. Illustrative non-viral vectors include, but are not limited to, plasmid, phage, yeast artificial chromosomes (YACs), Bacterial Artificial Chromosomes (BACs), and naked DNA vectors (e.g., by liposomal delivery), or synthetic nucleotide vectors (e.g., vectors that are generated by PCR methods or oligonucleotide synthesis, as known in the art). In embodiments of the invention, parvovirus and AAV vectors are used (in some instances, hybrid parvovirus or AAV vectors, as described above). Viral and non-viral delivery vectors are described in more detail hereinbelow.

The delivery vector comprises a heterologous nucleic acid sequence that encodes a secretory signal peptide. In embodiments of the invention, the secretory signal peptide is a fibronectin secretory signal peptide, which term includes modifications of naturally occurring sequences (as described in more detail below). In representative embodiments, the delivery vector further comprises a heterologous nucleic acid (as described herein) encoding a polypeptide of interest to be transferred to a target cell. The heterologous nucleic acid is operatively associated with the segment encoding the secretory signal peptide, such that upon transcription and translation a fusion polypeptide is produced containing the secretory signal sequence operably associated with (e.g., directing the secretion of) the polypeptide of interest.

According to the present invention, the secretory signal peptide is heterologous to (i.e., foreign or exogenous to) the polypeptide of interest. For example, if the secretory signal peptide is a fibronectin secretory signal peptide, the polypeptide of interest is not fibronectin.

In general, the secretory signal will be at the amino-terminus of the fusion polypeptide (i.e., the segment encoding the secretory signal sequence is 5' to the heterologous nucleic acid encoding the polypeptide of interest in the recombinant delivery vector construct). Alternatively, the secretory signal may be at the carboxy-terminus or embedded within the polypeptide of interest, as long as the secretory signal is operatively associated therewith and directs secretion of the polypeptide of interest (either with or without cleavage from the fusion polypeptide) from the cell.

The secretory signal is operatively associated with the polypeptide of interest so that the polypeptide is targeted to the secretory pathway. Alternatively stated, the secretory signal is operatively associated with the polypeptide such that the polypeptide is secreted from the cell at a higher level (i.e., a greater quantity) than in the absence of the secretory signal peptide. The degree to which the secretory signal peptide directs the secretion of the polypeptide is not critical, as long as it provides a desired level of secretion and/or regulation of expression of the polypeptide. Those skilled in the art will appreciate that when secretory proteins are over-expressed they often saturate the cellular secretion mechanisms and are retained within the cell. In general, typically at least about 20%, 30%, 40%, 50%, 70%, 80%, 85%, 90%, 95% or more of the polypeptide (alone and/or in the form of the fusion polypeptide) is secreted from the cell. In other embodiments, essentially all of the detectable polypeptide (alone and/or in the form of the fusion polypeptide) is secreted from the cell.

By the phrase "secreted from the cell", the polypeptide may be secreted into any compartment (e.g., fluid or space) outside of the cell including but not limited to: the interstitial space, blood, lymph, cerebrospinal fluid, kidney tubules, airway passages (e.g., alveoli, bronchioles, bronchia, nasal passages, etc.), the gastrointestinal tract (e.g., esophagus, stomach, small intestine, colon, etc.), vitreous fluid in the eye, and the cochlear endolymph, and the like.

Without wishing to be held to any particular theory of the invention, it is generally believed that secretory signal sequences direct the insertion of the nascent polypeptide into the endoplasmic reticulum from whence it is transported to the golgi, which then fuses with the cellular membrane to secrete the polypeptide from the cell. Typically, the secretory signal is cleaved from the polypeptide during processing, which is believed to occur in the endoplasmic reticulum. In the case of the fusion polypeptides of the present invention, it is not necessary that the secretory signal peptide be cleaved from the fusion polypeptide completely or at all. In some embodiments, the secretory signal peptide may be essentially completely cleaved; alternatively, with some polypeptides or in some cells, there may be incomplete cleavage or essentially no cleavage. While not wishing to be limited to any particular theory, in some embodiments it appears that retention (i.e., non-cleavage) of some or all of the secretory signal peptide stabilizes the resulting fusion polypeptide.

In exemplary embodiments, the secretory signal peptide is only partially removed from polypeptide, i.e., at least about one, two, three, four, five, six, seven, eight, nine, ten, twelve or even fifteen or more of the amino acid residues are retained by the secreted polypeptide. As illustrative examples, amino acids 22 (Val) to 32 (Arg), 23 (Arg) to 32 (Arg), 24 (Cys) to 32 (Arg), 25 (Thr) to 32 (Arg) or 26 (Glu) to 32 (Arg) of SEQ ID NO:2 may be retained by the secreted polypeptide.

As a further alternative, an exogenous peptidase cleavage site may be inserted into the fusion polypeptide, e.g., between the secretory signal sequence and the polypeptide of interest. In particular embodiments, an autoprotease (e.g., the foot and mouth disease virus 2A autoprotease) is inserted between the secretory signal peptide and the polypeptide of interest. In other embodiments, a protease recognition site that can be controlled by addition of exogenous protease is employed (e.g., Lys—Arg recognition site for trypsin, the Lys—Arg recognition site of the *Aspergillus* KEX2-like protease, the recognition site for a metalloprotease, the recognition site for a serine protease, and the like).

While not necessary, in particular embodiments of the invention, the heterologous nucleic acid encoding the polypeptide of interest will encode a mature form of the peptide (e.g., excluding any precursor sequences that are normally removed during processing of the polypeptide). Likewise, the polypeptide sequence may be modified to delete or inactivate native targeting or processing signals (for example, if they interfere with the desired level of secretion of the polypeptide according to the present invention).

The secretory signal sequences of the invention are not limited to any particular length as long as they direct the polypeptide of interest to the secretory pathway. In representative embodiments, the signal peptide is at least about 6, 8, 10 12, 15, 20, 25, 30 or 35 amino acids in length up to a length of about 40, 50, 60, 75, or 100 amino acids or longer.

As one skilled in the art will appreciate, secretory signal sequences are generally operative across species. Accordingly, the fibronectin secretory signal sequence of the invention may be derived from any species including, but not limited to, avians (e.g., chicken, duck, turkey, quail, etc.), mammals (e.g., human, simian, mouse, rat, bovine, ovine, caprine, equine, porcine, lagamorph, feline, canine, etc.), and other animals including *Caenorhabditis elegans, Xenopus laevis,* and *Danio rerio.* Examples of exemplary fibronectin secretory signal sequences include, but are not limited to, those illustrated in Table 1.

An exemplary nucleotide sequence encoding the fibronectin secretory signal sequence of *Rattus norvegicus* is found at GenBank accession number X15906 (the disclosure of which is incorporated herein by reference):

(SEQ ID NO:1)
5'-ATG CTC AGG GGT CCG GGA CCC GGG CGG CTG CTG CTG CTA GCA GTC CTG TGC CTG GGG ACA TCG GTG CGC TGC ACC GAA ACC GGG AAG AGC AAG AGG-3'.

This sequence encodes the polypeptide of SEQ ID NO:2 provided in Table 1 below.

The sequence of SEQ ID NO:1 does not include the nucleotide sequences that are 3' to the cleavage site (i.e., encode the amino acids C-terminal to the cleavage site). As those skilled in the art will appreciate, the fibronectin secretory signal peptide is typically cleaved from the fibronectin precursor by the cleavage action of an intracellular peptidase.

Accordingly, a further exemplary sequence also comprises the sequences 3' (and C-terminal) of the cleavage site (indicated by an arrow).

(SEQ ID NO:3)
5'-ATG CTC AGG GGT CCG GGA CCC GGG CGG CTG CTG CTG CTA GCA GTC CTG TGC CTG GGG ACA TCG GTG CGC TGC ACC GAA ACC GGG AAG AGC AAG AGG ↑ CAG GCT CAG CAA ATC GTG-3'.

This sequence encodes the polypeptide of SEQ ID NO:4 provided in Table 1 below. Those skilled in the art will appreciate that the secretory signal sequence may encode one, two, three, four, five or all six or more of the amino acids at the C-terminal side of the peptidase cleavage site.

As yet another illustrative sequence, the following is the nucleotide sequence encoding the secretory signal peptide of human fibronectin 1, transcript variant 1 (Accession No. NM_002026, nucleotides 268–345; the disclosure of Accession No. NM_002026 is incorporated herein by reference in its entirety).

(SEQ ID NO:14)
ATG CTT AGG GGT CCG GGG CCC GGG CTG CTG CTG CTG GCC GTC CAG TGC CTG GGG ACA GCG GTG CCC TCC ACG GGA GCC.

This sequence encodes the polypeptide of SEQ ID NO:5 provided in Table 1 below. Those skilled in the art will appreciate that additional amino acids (e.g., 1, 2, 3, 4, 5, 6 or more amino acids) on the carboxy-terminal side of the cleavage site may be included in the secretory signal sequence.

As still a further exemplary secretory signal sequence, the following is the nucleotide sequence encoding the secretory signal peptide of the *Xenopus laevis* fibronectin protein (Accession No. M77820, nucleotides 98–190; the disclosure of Accession No. M77820 incorporated herein by reference in its entirety).

(SEQ ID NO:15)
ATG CGC CGG GGG GCC CTG ACC GGG CTG CTC CTG GTC CTG TGC CTG AGT GTT GTG CTA CGT GCA GCC CCC TCT GCA ACA AGC AAG AAG CGC AGG

This sequence encodes the polypeptide of SEQ ID NO:6 provided in Table 1 below. Those skilled in the art will appreciate that additional amino acids (e.g., 1, 2, 3, 4, 5, 6 or more amino acids) on the carboxy-terminal side of the cleavage site may be included in the secretory signal sequence.

TABLE 1

| Species | Signal Sequence | |
|---|---|---|
| R. norvegicus | Met Leu Arg Gly Pro Gly Pro Gly Arg Leu Leu Leu Leu Ala Val Leu Cys Leu Gly Thr Ser Val Arg Cys Thr Glu Thr Gly Lys Ser Lys Arg | (SEQ ID NO:2) |
| R. norvegicus | Met Leu Arg Gly Pro Gly Pro Gly Arg Leu Leu Leu Leu Ala Val Leu Cys Leu Gly Thr Ser Val Arg Cys Thr Glu Thr Gly Lys Ser Lys Arg ↑ Leu Ala Leu Gln Ile Val | (SEQ ID NO:4) |
| H. sapiens | Met Leu Arg Gly Pro Gly Pro Gly Leu Leu Leu Leu Ala Val Gln Cys Leu Gly Thr Ala Val Pro Ser Thr Gly Ala | (SEQ ID NO:5) |
| X. laevis | Met Arg Arg Gly Ala Leu Thr Gly Leu Leu Leu Val Leu Cys Leu Ser Val Val Leu Arg Ala Ala Pro Ser Ala Thr Ser Lys Lys Arg Arg | (SEQ ID NO:6) |

The fibronectin secretory signal sequences of the invention encompass sequences from species other than those disclosed specifically herein as well as allelic variations and modifications thereof that retain secretory signal activity (e.g., confers a greater level [i.e., quantity] of secretion of the associated polypeptide than is observed in the absence of the secretory signal peptide, alternatively stated, has at least 50%, 70%, 80% or 90% or more of the secretory signal activity of the secretory signal peptides specifically disclosed herein or even has a greater level of secretory signal activity).

To illustrate, the fibronectin secretory signal sequences of the invention also include functional portions or fragments of the full-length secretory signal peptide (e.g., functional fragments of SEQ ID NO:2, SEQ ID NO:4, SEQ ID NO:5 and SEQ ID NO:6). The length of the fragment is not critical as long as it has secretory signal activity (e.g., confers a greater level [i.e., quantity] of secretion of the associated polypeptide than is observed in the absence of the secretory signal peptide). Illustrative fragments comprise at least 10, 12, 15, 18, 20, 25 or 27 contiguous amino acids of the full-length secretory signal peptide (e.g., fragments of SEQ ID NO:2, SEQ ID NO:4, SEQ ID NO:5 and SEQ ID NO:6). In embodiments of the invention, the functional fragment has at least about 50%, 70%, 80%, 90% or more secretory signal activity as compared with the sequences specifically disclosed herein or even has a greater level of secretory signal activity.

Likewise, those skilled in the art will appreciate that longer amino acid sequences (and nucleotide sequences encoding the same) that comprise the full-length fibronectin secretory signal (or fragment thereof with secretory signal activity) are encompassed by the term "fibronectin signal sequence" according to the present invention. Additional amino acids (e.g., 1, 2, 4, 6, 8, 10, 15 or even more amino acids) may be added to the fibronectin secretory signal sequence without unduly affecting secretory signal activity thereof (e.g., confers a greater level [i.e., quantity] of secretion of the associated polypeptide than is observed in the absence of the secretory signal peptide, alternatively stated, has at least about 50%, 70%, 80%, 90% or more secretory signal activity as compared with the sequences specifically disclosed herein or even has a greater level of secretory signal activity). For example, those skilled in the art will appreciate that peptide cleavage sites (described above) or restriction enzyme sites may be added, typically at either end of the secretory signal sequence. Additional sequences having other functions may also be fused to the fibronectin secretory signal sequence (e.g., sequences encoding FLAG sequences or poly-His tails that facilitate purification of the polypeptide or spacer sequences). Additionally sequences that encode polypeptides that enhance the stability of the polypeptide of interest may be added, e.g., sequences encoding maltose binding protein (MBP) or glutathione-S-transferase.

Other secretory signal sequences of the invention include, but are not limited to, the secretaory signal sequences from prepro-cathepsin L (e.g., GenBank Accession Nos. KHRTL, NP_037288; NP_034114, AAB81616, AAA39984, P07154, CAA68691; the disclosures of which are incorporated by reference in their entireties herein) and prepro-alpha 2 type collagen (e.g., GenBank Accession Nos. CAA98969, CAA26320, CGHU2S, NP_000080, BAA25383, P08123; the disclosures of which are incorporated by reference in their entireties herein) as well as allelic variations, modifications and functional fragments thereof (as discussed above with respect to the fibronectin secretory signal sequence).

Exemplary secretory signal sequences include for prepro-cathepsin L (*Rattus norvegicus*, MTPLLLLAVLCLGTALA [SEQ ID NO:22]; Accession No. CAA68691) and for pre-pro-alpha 2 type collagen (*Homo sapiens*, MLSFVDTRTLLLLAVTLCLATC [SEQ ID NO:23]; Accession No. CAA98969). Also encompassed are longer amino acid sequences comprising the full-length secretory signal sequence from preprocathepsin L and prepro-alpha 2 type collagen or functional fragments thereof (as discussed above with respect to the fibronectin secretory signal sequence). The secretory signal sequence can further be from any species as described above with respect to fibronectin secretory signal sequences.

A comparison of the fibronectin secretory signal sequence with the secretory signal sequences from the cathepsin L and alpha 2 type collagen precursors has resulted in identification of a core or canonical amino acid sequence: Leu Leu Leu Leu Ala Val Leu Cys Leu Gly Thr (SEQ ID NO:16).

Thus, the present invention further provides delivery vectors and chimeric nucleic acid sequences comprising the canonical amino acid sequence of SEQ ID NO:16.

Likewise, those skilled in the art will appreciate that the secretory signal sequences specifically disclosed herein will typically tolerate substitutions in the amino acid sequence and retain secretory signal activity (e.g., at least 50%, 70%, 80%, 90%, 95% or higher of the secretory signal activity the secretory signal peptides specifically disclosed herein). To identify secretory signal peptides of the invention other than those specifically disclosed herein, amino acid substitutions may be based on any characteristic known in the art, including the relative similarity or differences of the amino acid side-chain substituents, for example, their hydrophobicity, hydrophilicity, charge, size, and the like.

Amino acid substitutions other than those disclosed herein may be achieved by changing the codons of the DNA sequence (or RNA sequence), according to the following codon table:

TABLE 2

| Amino Acids | | | Codons |
|---|---|---|---|
| Alanine | Ala | A | GCA GCC GCG GCT |
| Cysteine | Cys | C | TGC TGT |
| Aspartic acid | Asp | D | GAC GAT |
| Glutamic acid | Glu | E | GAA GAG |
| Phenylalanine | Phe | F | TTC TTT |
| Glycine | Gly | G | GGA GGC GGG GGT |
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |

TABLE 2-continued

| Amino Acids | | | Codons |
|---|---|---|---|
| Serine | Ser | S | AGC ACT TCA TCC TCG TCT |
| Threonine | Thr | T | ACA ACC ACG ACT |
| Valine | Val | V | GTA GTC GTG GTT |
| Tryptophan | Trp | W | TGG |
| Tyrosine | Tyr | Y | TAC TAT |

In identifying other secretory signal sequences, the hydropathic index of amino acids may be considered. The importance of the hydropathic amino acid index in conferring interactive biologic function on a protein is generally understood in the art (see, Kyte and Doolittle, (1982) *J. Mol. Biol.* 157:105; incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, Id.), these are:

isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Accordingly, the hydropathic index of the amino acid (or amino acid sequence) may be considered when modifying the fibronectin secretory signal peptides specifically disclosed herein.

It is also understood in the art that the substitution of amino acids can be made on the basis of hydrophilicity. U.S. Pat. No. 4,554,101 (incorporated herein by reference in its entirety) states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (−0.4); proline (−0.5±1); alanine (−0.5), histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Thus, the hydrophilicity of the amino acid (or amino acid sequence) may be considered when identifying additional fibronectin secretory signal peptides beyond those specifically disclosed herein.

In embodiments of the invention, the nucleic acid encoding the secretory signal sequence will hybridize to the nucleic acid sequences encoding the secretory signal peptides specifically disclosed herein under standard conditions as known by those skilled in the art.

For example, hybridization of such sequences may be carried out under conditions of reduced stringency, medium stringency or even stringent conditions (e.g., conditions represented by a wash stringency of 35–40% Formamide with 5× Denhardt's solution, 0.5% SDS and 1×SSPE at 37° C.; conditions represented by a wash stringency of 40–45% Formamide with 5× Denhardt's solution, 0.5% SDS, and 1×SSPE at 42° C.; and conditions represented by a wash stringency of 50% Formamide with 5× Denhardt's solution, 0.5% SDS and 1×SSPE at 42° C., respectively) to the nucleic acid sequences encoding the secretory signal sequences specifically disclosed herein. See, e.g., Sambrook et al., *Molecular Cloning, A Laboratory Manual* (2d Ed. 1989) (Cold Spring Harbor Laboratory).

Alternatively stated, nucleic acid sequences encoding the secretory signal peptides of the invention have at least about 60%, 70%, 80%, 90%, 95%, 97% or higher sequence identity with the nucleic acid sequences specifically disclosed herein (or active fragments thereof, as described above) and encode peptides having secretory signal activity (e.g., confer a greater level [i.e., quantity] of secretion of the associated polypeptide than is observed in the absence of the secretory signal peptide, alternatively stated, have at least 50%, 70%, 80%, 90%, 95% or higher of the secretory signal activity of the secretory signal peptides specifically disclosed herein).

Further, it will be appreciated by those skilled in the art that there can be variability in the polynucleotides that encode the secretory signal peptides of the present invention due to the degeneracy of the genetic code. The degeneracy of the genetic code, which allows different nucleic acid sequences to code for the same polypeptide, is well known in the literature (See, e.g., Table 2).

Likewise, the secretory signal sequences of the invention include polypeptides that have at least about 60%, 70%, 80%, 90%, 95%, 97% or higher amino acid sequence identity with the polypeptide sequences specifically disclosed herein (or fragments thereof, as described above) and have secretory signal activity (e.g., at least 50%, 70%, 80%, 90%, 95% or higher of the secretory signal activity of the secretory signal peptides specifically disclosed herein).

As is known in the art, a number of different programs can be used to identify whether a nucleic acid or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch, *J. Mol. Biol.* 48,443 (1970), by the search for similarity method of Pearson & Lipman, *Proc. Natl. Acad. Sci. USA* 85,2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12, 387–395 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35, 351–360 (1987); the method is similar to that described by Higgins & Sharp, *CABIOS* 5, 151–153 (1989).

Another example of a useful algorithm is the BLAST algorithm, described in Altschul et al., *J. Mol. Biol.* 215, 403–410, (1990) and Karlin et al., *Proc. Natl. Acad. Sci. USA* 90, 5873–5787 (1993). A particularly useful BLAST program is the WU-BLAST-2 program which was obtained from Altschul et al., *Methods in Enzymology*, 266, 460–480 (1996). WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. *Nucleic Acids Res.* 25, 3389–3402.

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity with respect to the coding sequence of the secretory signal peptides disclosed herein is defined as the percentage of nucleotide residues in the candidate sequence that are identical with the nucleotides in the secretory signal peptide specifically disclosed herein.

The alignment may include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

III. Recombinant Delivery Vectors.

The delivery vectors produced according to the present invention are useful for the delivery of nucleic acids to cells in vitro, ex vivo, and in vivo. In particular, the delivery vectors can be advantageously employed to deliver or transfer nucleic acids to animal, more preferably mammalian, cells. Any heterologous nucleic acid sequence(s) may be provided with a delivery vector according to the present invention. Nucleic acids of interest include nucleic acids encoding polypeptides, preferably therapeutic (e.g., for medical or veterinary uses) or immunogenic (e.g., for vaccines) polypeptides.

In general, the secretory signal peptide of the invention is heterologous to the polypeptide encoded by the delivery vector, e.g., in the case of a fibronectin secretory signal, the heterologous nucleic acid does not encode fibronectin.

Therapeutic polypeptides include, but are not limited to, cystic fibrosis transmembrane regulator protein (CFTR), dystrophin (including the protein product of dystrophin mini-genes, see, e.g, Vincent et al., (1993) *Nature Genetics* 5:130), utrophin (Tinsley et al., (1996) *Nature* 384:349), clotting factors (e.g., Factor XIII, Factor IX, Factor X, etc.), erythropoietin, angiostatin, endostatin, catalase, tyrosine hydroxylase, superoxide dismutase, leptin, the LDL receptor, lipoprotein lipase, ornithine transcarbamylase, β-globin, α-globin, spectrin, $α_1$-antitrypsin, adenosine deaminase, hypoxanthine guanine phosphoribosyl transferase, β-glucocerebrosidase, sphingomyelinase, lysosomal hexosaminidase, branched-chain keto acid dehydrogenase, RP65 protein, cytokines (e.g., α-interferon, β-interferon, interferon-γ, interleukin-2, interleukin-4, granulocyte-macrophage colony stimulating factor, lymphotoxin, and the like), peptide growth factors and hormones (e.g., somatotropin, somatostatin, insulin, insulin-like growth factors 1 and 2, platelet derived growth factor, epidermal growth factor, fibroblast growth factor, nerve growth factor, neurotrophic factor −3 and −4, transforming growth factor −α and −β, and the like), receptors (e.g., the tumor necrosis growth factor receptor), enzymes, monoclonal antibodies (including single chain monoclonal antibodies or Fab fragment; an exemplary Mab is the herceptin Mab).

In particular embodiments, the heterologous nucleic acid encodes a neuropeptide. Illustrative neuropeptides include, but are not limited to, galanin (e.g., to treat epilepsy or eating/weight disorders), neuropeptide Y or a receptor specific neuropeptide Y variant (e.g., to treat epilepsy or a weight disorder), brain-derived neurotrophic factor (e.g., to treat Parkinson's Disease), glial cell derived growth factor (e.g., to treat Parkinson's Disease), neurotrophic factor −3 and −4 (e.g., to treat Parkinson's disease), cholecystokinin (e.g., to treat epilepsy), thyrotropin-releasing hormone (e.g., to treat psychiatric disorders), neurotensin (e.g., to treat psychiatric disorders), oxytocin (e.g., to treat psychiatric disorders), acidic fibroblast growth factor, basic fibroblast growth factor, nerve growth factor (e.g., to treat Parkinson's Disease), met-enkephalin (e.g., to treat pain), leu-enkephalin (e.g., to treat pain), dynorphin (e.g., to treat pain), β-endorphin (e.g., to treat pain), leptin (e.g., to treat weight disorders), a semaphorin peptide (e.g., to promote axonal guidance), and somatostatin (e.g., to treat somatostatin sensitive brain tumors or acromegaly).

Other heterologous nucleic acid sequences of interest for delivery to the CNS include tyrosine hydroxylase (e.g., to treat Parkinson's disease), aromatic amino acid decarboxylase (e.g., to treat Parkinson's disease), superoxide dismutase (e.g., to treat Parkinson's Disease or amyotrophic lateral sclerosis), catalase (e.g., to treat Parkinson's Disease), glutathione peroxidase (e.g., to treat Parkinson's disease), adenosine A-1 receptor (e.g., to treat epilepsy), GABA-A receptor (e.g., to treat epilepsy), and glutamate decarboxylase (e.g., to treat epilepsy).

Further illustrative heterologous nucleotide sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), and any other polypeptide that has a therapeutic effect in a subject in need thereof. Other exemplary anti-cancer or anti-tumor agents include antibodies (including antibody Fab fragments), endostatin, angiostatin, thymidine kinase and cytokines (e.g., interferons).

The heterologous nucleic acid sequence may also encode a polypeptide associated with a mucopolysaccharide disease, including but not limited to: Hurler Syndrome (MPS III; α-L-iduronidase), Scheie Syndrome (MPS IS; α-L-iduronidase), Hurler-Scheie Syndrome (MPS IH/S; α-L- iduronidase), Hunter Syndrome (MPS II; iduronate sulfatase), Sanfilippo A Syndrome (MPS IIIA; heparan N-sulfatase), Sanfilippo B Syndrome (MPS IIIB; α-N-acetylglucosaminidase), Sanfilippo C Syndrome (MPS IIIC; acetyl-CoA-glucosaminide acetyltransferase), Sanfilippo D Syndrome (MPS IIID; N-acetylglucosamine-6-sulfatase), Morquio A disease (MPS IVA; galactosamine-6-sulfatase), Morquio B disease (MPS IV B; β-galactosidase), Maroteaux-Lamy disease (MPS VI; arylsulfatase B), and Sly Syndrome (MPS VII; β-glucuronidase).

Heterologous nucleic acid sequences encoding polypeptides include those encoding reporter polypeptides (e.g., an enzyme). Reporter polypeptides are known in the art and include, but are not limited to, Green Fluorescent Protein, β-galactosidase, luciferase, alkaline phosphatase, and chloramphenicol acetyltransferase gene.

The present invention may be used to provide a delivery vector to express an immunogenic polypeptide in a subject, e.g., for vaccination. The nucleic acid may encode any immunogen of interest known in the art including, but not limited to, immunogens from human immunodeficiency virus, influenza virus, gag proteins, tumor antigens, cancer antigens, bacterial antigens, viral antigens, and the like.

An immunogenic polypeptide, or immunogen, may be any polypeptide suitable for protecting the subject against a pathogen, including but not limited to microbial, bacterial, protozoal, parasitic, and viral pathogens. For example, the immunogen may be an orthomyxovirus immunogen (e.g., an influenza virus immunogen, such as the influenza virus hemagglutinin (HA) surface protein or the influenza virus nucleoprotein gene), or an equine influenza virus immunogen), or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogen may also be an arenavirus immunogen (e.g., Lassa fever virus immunogen, such as the Lassa fever virus nucleocapsid protein gene and the Lassa fever envelope glycoprotein gene), a poxvirus immunogen (e.g., vaccinia, such as the vaccinia L1 or L8 genes), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP genes), a bunyavirus immunogen (e.g., RVFV, CCHF, and SFS viruses), or a coronavirus immunogen (e.g., an infectious human coronavirus immunogen, such as the human coronavirus envelope glycoprotein gene, or a porcine transmissible gastroenteritis virus immunogen, or an avian infectious bronchitis virus immunogen). The immunogen may further be a polio immunogen, herpes antigen (e.g., CMV, EBV, HSV immunogens) mumps immunogen, measles immunogen, rubella immunogen, diptheria toxin or other diptheria immunogen, pertussis antigen, hepatitis (e.g., hepatitis A or hepatitis B) immunogen, or any other vaccine immunogen known in the art.

Alternatively, the immunogen may be any tumor or cancer cell antigen. Preferably, the tumor or cancer antigen is expressed on the surface of the cancer cell. Exemplary cancer and tumor cell antigens are described in S. A. Rosenberg, (1999) *Immunity* 10:281). Other illustrative cancer and tumor antigens include, but are not limited to: BRCA1 gene product, BRCA2 gene product, gp100, tyrosinase, GAGE-½, BAGE, RAGE, NY-ESO-1, CDK-4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515); Kawakami et al., (1994) *J. Exp. Med.,* 180:347); Kawakami et al., (1994) *Cancer Res.* 54:3124), including MART-1 (Coulie et al., (1991) *J. Exp. Med.* 180:35), gp100 (Wick et al., (1988) *J. Cutan. Pathol.* 4:201) and MAGE antigen, MAGE-1, MAGE-2 and MAGE-3 (Van der Bruggen et al., (1991) *Science,* 254:1643); CEA, TRP-1, TRP-2, P-15 and tyrosinase (Brichard et al., (1993) *J. Exp. Med.* 178:489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) *Ann. Rev. Biochem.* 62:623); mucin antigens (international patent publication WO 90/05142); telomerases; nuclear matrix proteins; prostatic acid phosphatase; papilloma virus antigens; and antigens associated with the following cancers: brain tumors and other cancers of the CNS, melanomas, metastases, adenocarcinoma, thymoma, lymphoma, sarcoma, lung cancer, liver cancer, colon cancer, non-Hodgkins lymphoma, Hodgkins lymphoma, leukemias, uterine cancer, breast cancer, prostate cancer, ovarian cancer, cervical cancer, bladder cancer, kidney cancer, pancreatic cancer and others cancers as known in the art (see, e.g., Rosenberg, (1 996) *Ann. Rev. Med.* 47:481–91).

Alternatively, the heterologous nucleotide sequence may encode any polypeptide that is desirably produced in a cell in vitro, ex vivo, or in vivo. For example, the delivery vector may be introduced into cultured cells and the expressed gene product isolated therefrom. Such an in vitro system can be used to produce quantities of a polypeptide (e.g., a hormone, growth factor, industrial enzyme, antibody, a therapeutic polypeptide, or any other polypeptide of interest). Alternatively, the polypeptide may be produced in an animal in vivo. According to this embodiment, the animal is used essentially as a bioreactor to produce the polypeptide.

It will be understood by those skilled in the art that the heterologous nucleic acid sequence(s) of interest may be operably associated with appropriate control sequences. For example, the heterologous nucleic acid may be operably associated with expression control elements, such as transcription/translation control signals, origins of replication, polyadenylation signals, and internal ribosome entry sites (IRES), promoters, enhancers, and the like.

It will further be appreciated that a variety of promoter/enhancer elements may be used depending on the level and tissue-specific expression desired. The promoter/enhancer may be constitutive or inducible, depending on the pattern of expression desired. The promoter/enhancer may be native or foreign and can be a natural or a synthetic sequence. By foreign, it is intended that the transcriptional initiation region is not found in the wild-type host into which the transcriptional initiation region is introduced.

Promoter/enhancer elements that are native to the target cell or subject to be treated are most preferred. Also preferred are promoters/enhancer elements that are native to the heterologous nucleic acid sequence. The promoter/enhancer element is chosen so that it will function in the target cell(s) of interest. Mammalian promoter/enhancer elements are also preferred. The promoter/enhance element may be constitutive or inducible.

Exemplary constitutive promoters include, but are not limited to a β-actin promoter, a cytomegalovirus promoter, a cytomegalovirus/β-actin hybrid promoter, and a Rous sarcoma virus promoter.

Inducible expression control elements are generally employed in those applications in which it is desirable to provide regulation over expression of the heterologous nucleic acid sequence(s). Inducible promoters/enhancer elements for gene delivery include brain-specific, muscle specific (including cardiac, skeletal and/or smooth muscle), liver specific, bone marrow specific, pancreatic specific, spleen specific, and lung specific promoter/enhancer elements.

In particular embodiments, the promoter/enhancer is functional in cells or tissue of the CNS, and may even be specific to cells or tissues of the CNS. Such promoters/enhancers include but are not limited to promoters/enhancers that function in the eye (e.g., retina and cornea), neurons (e.g., the neuron specific enolase, AADC, synapsin, or serotonin receptor promoter), glial cells (e.g., S100 or glutamine synthase promoter), and oligodendricytes. Other promoters which have been demonstrated to direct synthesis in the CNS include, but are not limited to, myelin basic protein (MBP) promoter (Tani et al., (1996) *J. Clin. Invest.* 98:529), and the prion promoter (Loftus et al., (2002) *Hum. Mol. Genet.* 11:3107).

Brain-specific promoters include BHLHB5 (Xu et al., (2002) *Genomics* 80:311), 14-3-3 protein promoter (Toyooka et al., (2002) *Brain Res. Mol. Brain Res.* 100:13), fibroblast growth factor-1β promoter (Chiu et al., (2001) *Prog. Nucleic Acid Res. Mol. Biol.* 70:155), glial fibrillary acidic protein gene promoter (Shi et al., (2001) *Proc. Natl. Acad. Sci. USA* 98:12754), N-methyl-D-aspartate receptor 2A subunit promoter (Desai et al., (2002) *J. Biol. Chem.* 277:46374), synapsin-I promoter (Morimoto et al., (2002) *J. Biol. Chem.* 277:33235), proteolipid protein promoter (Kahle et al., (2002) *EMBO Rep.* 3:583), platelet-derived growth factor-β promoter (Georgopoulos et al., (2002) *Biochemistry* 41:9293) and tyrosine hydroxylase promoter (Kessler et al., (2003) *Brain Res. Mol. Brain Res.* 112:8).

Other inducible promoter/enhancer elements include hormone-inducible and metal-inducible elements, and other promoters regulated by exogenously supplied compounds, including without limitation, the zinc-inducible metallothionein (MT) promoter; the dexamethasone (Dex)-inducible mouse mammary tumor virus (MMTV) promoter; the T7 polymerase promoter system (see WO 98/10088); the ecdysone insect promoter (No et al., (1996) *Proc. Natl. Acad. Sci. USA* 93:3346); the tetracycline-repressible system (Gossen et al., (1992) *Proc. Natl. Acad. Sci. USA* 89:5547); the tetracycline-inducible system (Gossen et al., (1995) *Science* 268:1766; see also Harvey et al., (1998) *Curr. Opin. Chem. Biol.* 2:512); the RU486-inducible system (Wang et al., (1997) *Nat. Biotech.* 15:239; Wang et al., (1997) *Gene Ther.*, 4:432); and the rapamycin-inducible system (Magari et al., (1997) *J. Clin. Invest.* 100:2865).

In embodiments wherein the heterologous nucleic acid sequence(s) will be transcribed and then translated in the target cells, specific initiation signals are generally required for efficient translation of inserted protein coding sequences. These exogenous translational control sequences, which may include the ATG initiation codon and adjacent sequences, can be of a variety of origins, both natural and synthetic.

It will be apparent to those skilled in the art that any suitable vector can be used to deliver the heterologous nucleic acids. The choice of delivery vector can be made based on a number of factors known in the art, including age and species of the target host, in vitro vs. in vivo delivery, level and persistence of expression desired, intended purpose (e.g., for therapy or polypeptide production), the target cell or organ, route of delivery, size of the isolated nucleic acid, safety concerns, and the like.

Suitable vectors include virus vectors (e.g., retrovirus, alphavirus; vaccinia virus; adenovirus, adeno-associated virus, or herpes simplex virus), lipid vectors, poly-lysine vectors, synthetic polyamino polymer vectors that are used with nucleic acid molecules, such as plasmids, and the like.

Any viral vector that is known in the art can be used in the present invention. Examples of such viral vectors include, but are not limited to vectors derived from: Adenoviridae; Birnaviridae; Bunyaviridae; Caliciviridae, Capillovirus group; Carlavirus group; Carmovirus virus group; Group Caulimovirus; Closterovirus Group; Commelina yellow mottle virus group; Comovirus virus group; Coronaviridae; PM2 phage group; Corcicoviridae; Group Cryptic virus; group Cryptovirus; Cucumovirus virus group Family ([PHgr]6 phage group; Cysioviridae; Group Carnation ringspot; Dianthovirus virus group; Group Broad bean wilt; Fabavirus virus group; Filoviridae; Flaviviridae; Furovirus group; Group Germinivirus; Group Giardiavirus; Hepadnaviridae; Herpesviridae; Hordeivirus virus group; Illarvirus virus group; lnoviridae; Iridoviridae; Leviviridae; Lipothrixviridae; Luteovirus group; Marafivirus virus group; Maize chlorotic dwarf virus group; icroviridae; Myoviridae; Necrovirus group; Nepovirus virus group; Nodaviridae; Orthomyxoviridae; Papovaviridae; Paramyxoviridae; Parsnip yellow fleck virus group; Partitiviridae; Parvoviridae; Pea enation mosaic virus group; Phycodnaviridae; Picomaviridae; Plasmaviridae; Prodoviridae; Polydnaviridae; Potexvirus group; Potyvirus; Poxviridae; Reoviridae; Retroviridae; Rhabdoviridae; Group Rhizidiovirus; Siphoviridae; Sobemovirus group; SSV 1-Type Phages; Tectiviridae; Tenuivirus; Tetraviridae; Group Tobamovirus; Group Tobravirus; Togaviridae; Group Tombusvirus; Group Tobovirus; Totiviridae; Group Tymovirus; and Plant virus satellites.

Protocols for producing recombinant viral vectors and for using viral vectors for nucleic acid delivery can be found in *Current Protocols in Molecular Biology,* Ausubel, F. M. et al. (eds.) Greene Publishing Associates, (1989) and other standard laboratory manuals (e.g., Vectors for Gene Therapy. In: *Current Protocols in Human Genetics.* John Wiley and Sons, Inc.: 1997).

Particular examples of viral vectors are those previously employed for the delivery of nucleic acids including, for example, retrovirus, lentivirus, adenovirus, AAV and other parvoviruses, herpes virus, and poxvirus vectors.

The term "parvovirus" as used herein encompasses the family Parvoviridae, including autonomously-replicating parvoviruses and dependoviruses. The autonomous parvoviruses include members of the genera *Parvovirus, Erythrovirus, Densovirus, Iteravirus,* and *Contravirus.* Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, and B19 virus, and any other virus classified by the International Committee on Taxonomy of Viruses (ICTV) as a parvovirus.

Other autonomous parvoviruses are known to those skilled in the art. See, e.g., BERNARD N. FIELDS et al., VIROLOGY, volume 2, chapter 69 (4th ed., Lippincott-Raven Publishers).

The genus *Dependovirus* contains the adeno-associated viruses (AAV), including but not limited to, AAV type 1, AAV type 2, AAV type 3, AAV type 4, AAV type 5, AAV type 6, AAV type 7, AAV type 8, avian AAV, bovine AAV, canine AAV, equine AAV, and ovine AAV, and any other virus classified by the International Committee on Taxonomy of Viruses (ICTV) as a dependovirus (e.g., AAV). See, e.g., BERNARD N. FIELDS et al., VIROLOGY, volume 2, chapter 69 (4th ed., Lippincott-Raven Publishers).

In particular embodiments, the delivery vector comprises an AAV capsid including but not limited to a capsid from AAV type 1, AAV type 2, AAV type 3, AAV type 4, AAV type 5, AAV type 6, AAV type 7 or AAV type 8.

The genomic sequences of the various serotypes of AAV and the autonomous parvoviruses, as well as the sequences of the terminal repeats (TRs), Rep proteins, and capsid subunits are known in the art. Such sequences may be found in the literature or in public databases such as GenBank. See, e.g., GenBank Accession Numbers NC 002077, NC 001401, NC 001729, NC 001863, NC 001829, NC 001862, NC 000883, NC 001701, NC 001510, AF063497, U89790, AF043303, AF028705, AF028704, J02275, J01901, J02275, X01457, AF288061, AH009962, AY028226, AY028223, NC 001358, NC 001540, AF513851, AF513852; the disclosures of which are incorporated herein in their entirety. See also, e.g., Srivistava et al., (1983) J. Virology 45:555; Chiorini et al., (1998) J. Virology 71:6823; Chiorini et al., (1999) J. Virology 73:1309; Bantel-Schaal et al., (1999) J. Virology 73:939; Xiao et al., (1999) J. Virology 73:3994; Muramatsu et al., (1996) Virology 221:208; Shade et al., (1986) J. Virol. 58:921; Gao et al., (2002) Proc. Nat. Acad. Sci. USA 99:11854; international patent publications WO 00/28061, WO 99/61601, WO 98/11244; U.S. Pat. No. 6,156,303; the disclosures of which are incorporated herein in their entirety. An early description of the AAV1, AAV2 and AAV3 terminal repeat sequences is provided by Xiao, X., (1996), "Characterization of Adeno-associated virus (AAV) DNA replication and integration," Ph.D. Dissertation, University of Pittsburgh, Pittsburgh, Pa. (incorporated herein it its entirety).

The parvovirus AAV particles of the invention may be "hybrid" parvovirus or AAV particles in which the viral terminal repeats and viral capsid are from different parvoviruses or AAV, respectively. Hybrid parvoviruses are described in more detail in international patent publication WO 00/28004; Chao et al., (2000) Molecular Therapy 2:619; and Chao et al., (2001) Mol. Ther. 4:217 (the disclosures of which are incorporated herein in their entireties). In representative embodiments, the viral terminal repeats and capsid are from different serotypes of AAV (i.e., a "hybrid AAV particle").

The parvovirus or AAV capsid may further be a "chimeric" capsid (e.g., containing sequences from different parvoviruses, preferably different AAV serotypes) or a "targeted" capsid (e.g., having a directed tropism) as described in international patent publication WO 00/28004.

Further, the parvovirus or AAV vector may be a duplexed parvovirus particle or duplexed AAV particle as described in international patent publication WO 01/92551.

Adeno-associated viruses (AAV) have been employed as nucleic acid delivery vectors. For a review, see Muzyczka et al. Curr. Topics in Micro. and Immunol. (1992) 158:97–129). AAV are parvoviruses and have small icosahedral virions, 18–26 nanometers in diameter and contain a single stranded genomic DNA molecule 4–5 kilobases in size. The viruses contain either the sense or antisense strand of the DNA molecule and either strand is incorporated into the virion. Two open reading frames encode a series of Rep and Cap polypeptides. Rep polypeptides (Rep50, Rep52, Rep68 and Rep78) are involved in replication, rescue and integration of the AAV genome, although significant activity can be observed in the absence of all four Rep polypeptides. The Cap proteins (VP1, VP2, VP3) form the virion capsid. Flanking the rep and cap open reading frames at the 5' and 3' ends of the genome are 145 basepair inverted terminal repeats (ITRs), the first 125 basepairs of which are capable of forming Y- or T-shaped duplex structures. It has been shown that the ITRs represent the minimal cis sequences required for replication, rescue, packaging and integration of the AAV genome. All other viral sequences are dispensable and may be supplied in trans (Muzyczka, (1992) Curr. Topics Microbiol. Immunol. 158:97).

AAV are among the few viruses that can integrate their DNA into non-dividing cells, and exhibit a high frequency of stable integration into human chromosome 19 (see, for example, Flotte et al. (1992) Am. J. Respir. Cell. Mol. Biol. 7:349–356; Samulski et al., (1989) J Virol. 63:3822–3828; and McLaughlin et al., (1989) J. Virol. 62:1963–1973). A variety of nucleic acids have been introduced into different cell types using AAV vectors (see, for example, Hermonat et al., (1984) Proc. Nat. Acad. Sci. USA 81:6466–6470; Tratschin et al., (1985) Mol. Cell. Biol. 4:2072–2081; Wondisford et al., (1988) Mol. Endocrinol. 2:32–39; Tratschin et al., (1984) J. Virol. 51:611–619; and Flotte et al., (1993) J. Biol. Chem. 268:3781–3790).

Generally, a rAAV vector genome will only retain the terminal repeat (TR) sequence(s) so as to maximize the size of the transgene that can be efficiently packaged by the vector. The structural and non-structural protein coding sequences may be provided in trans (e.g., from a vector, such as a plasmid, or by stably integrating the sequences into a packaging cell). Typically, the rAAV vector genome comprises at least one AAV terminal repeat, more typically two AAV terminal repeats, which generally will be at the 5' and 3' ends of the heterologous nucleotide sequence(s).

An "AAV terminal repeat" may be from any AAV including serotypes 1, 2, 3, 4, 5, 6, 7 and 8. The term "terminal repeat" includes synthetic sequences that function as an AAV inverted terminal repeat, such as the "double-D sequence" as described in U.S. Pat. No. 5,478,745 to Samulski et al., the disclosure of which is incorporated in its entirety herein by reference. The AAV terminal repeats need not have a wild-type terminal repeat sequence (e.g., a wild-type sequence may be altered by insertion, deletion, truncation or missense mutations), as long as the terminal repeat mediates the desired functions, e.g., replication, virus packaging, integration, and/or provirus rescue, and the like. Examples of altered terminal repeat sequences are disclosed by international patent publication WO 01/92551 (the disclosure of which is incorporated herein by reference in its entirety).

As used herein, AAV "rep coding sequences" indicate the nucleic acid sequences that encode the AAV non-structural proteins that mediate viral replication and the production of new virus particles. The AAV replication genes and proteins have been described, e.g., in BERNARD N. FIELDS et al., VIROLOGY, volume 2, chapter 69 (4th ed., Lippincott-Raven Publishers).

As used herein, the AAV "cap coding sequences" encode the structural proteins that form a functional AAV capsid (i.e., can package DNA and infect target cells). Typically, the cap coding sequences will encode all of the AAV capsid subunits, but less than all of the capsid subunits may be encoded as long as a functional capsid is produced. The capsid structure of AAV are described in more detail in BERNARD N. FIELDS et al., VIROLOGY, volume 2, chapter 69 (4th ed., Lippincott-Raven Publishers.

With respect to a rAAV delivery vector, the recombinant vector genome is generally about 80% to about 105% of the size of the wild-type genome and comprises an appropriate packaging signal. To facilitate packaging into an AAV capsid, the genome is preferably approximately 5.2 kb in size or less. In other embodiments, the genome is preferably greater than about 3.6, 3.8, 4.0, 4.2, or 4.4 kb in length and/or less than about 5.4, 5.2, 5.0 or 4.8 kb in length. Alternatively stated, the heterologous nucleotide sequence(s) will typically be less than about 5 kb in length (more preferably less than about 4.8 kb, still more preferably less than about 4.4 kb in length, yet more preferably less than about 4.2 kb in length) to facilitate packaging of the recombinant genome by the AAV capsid.

Any suitable method known in the art can be used to produce AAV vectors expressing the nucleic acids of this invention, for example, coding sequences for a carboxyl terminal deleted $G_M$ subunit (see, e.g., U.S. Pat. Nos. 5,139,941; 5,858,775; 6,146,874 for illustrative methods). In one particular method, AAV stocks can be produced by co-transfection of a rep/cap vector encoding AAV packaging functions and the template encoding the AAV vDNA into human cells infected with the helper adenovirus (Samulski et al., (1989) *J. Virology* 63:3822).

In other particular embodiments, the adenovirus helper virus is a hybrid helper virus that encodes AAV Rep and/or capsid proteins. Hybrid helper Ad/AAV vectors expressing AAV rep and/or cap genes and methods of producing AAV stocks using these reagents are known in the art (see, e.g., U.S. Pat. Nos. 5,589,377; and 5,871,982, 6,251,677; and 6,387,368). Preferably, the hybrid Ad of the invention expresses the AAV capsid proteins (i.e., VP1, VP2, and VP3). Alternatively, or additionally, the hybrid adenovirus can express one or more of AAV Rep proteins (i.e., Rep40, Rep52, Rep68 and/or Rep78). The AAV sequences can be operatively associated with a tissue-specific or inducible promoter.

The AAV rep and/or cap genes can alternatively be provided by a packaging cell that stably expresses the genes (see, e.g., Gao et al., (1998) *Human Gene Therapy* 9:2353; Inoue et al., (1998) *J. Virol.* 72:7024; U.S. Pat. No. 5,837,484; WO 98/27207; U.S. Pat. No. 5,658,785; WO 96/17947).

In other embodiments of the present invention, the delivery vector is an adenovirus vector. In representative embodiments, the adenovirus is a serogroup C adenovirus, still more preferably the adenovirus is serotype 2 (Ad2) or serotype 5 (Ad5). An adenovirus vector genome or rAd vector genome will typically comprise the Ad terminal repeat sequences and packaging signal. Generally, the adenovirus vector genome is most stable at sizes of about 28 kb to 38 kb (approximately 75% to 105% of the native genome size).

The various regions of the adenovirus genome have been mapped and are understood by those skilled in the art (see, e.g., FIELDS et al., VIROLOGY, volume 2, chapters 67 and 68 (3d ed., Lippincott-Raven Publishers). The genomic sequences of the various Ad serotypes, as well as the nucleotide sequence of the particular coding regions of the Ad genome, are known in the art and can be accessed, e.g., from GenBank and NCBI (see, e.g., GenBank Accession Nos. J0917, M73260, X73487, AF108105, L19443, NC 003266 and NCBI Accession Nos. NC 001405, NC 001460, NC 002067, NC 00454).

Normally adenoviruses bind to a cell surface receptor (CAR) of susceptible cells via the knob domain of the fiber protein on the virus surface. The fiber knob receptor is a 45 kDa cell surface protein which has potential sites for both glycosylation and phosphorylation. (Bergelson et al., (1997), *Science* 275:1320–1323). A secondary method of entry for adenovirus is through integrins present on the cell surface. Arginine-Glycine-Aspartic Acid (RGD) sequences of the adenoviral penton base protein bind integrins on the cell surface.

The adenovirus genome can be manipulated such that it encodes and expresses a nucleic acid of interest but is inactivated in terms of its ability to replicate in a normal lytic viral life cycle. See, for example, Berkner et al. (1988) *BioTechniques* 6:616; Rosenfeld et al. (1991) *Science* 252: 431–434; and Rosenfeld et al. (1992) *Cell* 68:143–155. Representative adenoviral vectors derived from the adenovirus strain Ad type 5 d1324 or other strains of adenovirus (e.g., Ad2, Ad3, Ad7 etc.) are known to those skilled in the art.

Recombinant adenoviruses can be advantageous in certain circumstances in that they are not capable of infecting nondividing cells and can be used to infect a wide variety of cell types, including epithelial cells. Furthermore, the virus particle is relatively stable and amenable to purification and concentration, and can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., as occurs with retroviral DNA). Moreover, the carrying capacity of the adenoviral genome for foreign DNA is large relative to other delivery vectors (Haj-Ahmand and Graham (1986) *J. Virol.* 57:267).

Another vector for use in the present invention comprises Herpes Simplex Virus (HSV). Herpes simplex virions have an overall diameter of 150 to 200 nm and a genome consisting of one double-stranded DNA molecule that is 120 to 200 kilobases in length. Glycoprotein D (gD) is a structural component of the HSV envelope that mediates virus entry into host cells. The initial interaction of HSV with cell surface heparin sulfate proteoglycans is mediated by another glycoprotein, glycoprotein C (gC) and/or glycoprotein B (gB). This is followed by interaction with one or more of the viral glycoproteins with cellular receptors. It has been shown that glycoprotein D of HSV binds directly to Herpes virus entry mediator (HVEM) of host cells. HVEM is a member of the tumor necrosis factor receptor superfamily (Whitbeck et al., (1997), *J. Virol;* 71:6083–6093). Finally, gD, gB and the complex of gH and gL act individually or in combination to trigger pH-independent fusion of the viral envelope with the host cell plasma membrane. The virus itself is transmitted by direct contact and replicates in the skin or mucosal membranes before infecting cells of the nervous system for which HSV has particular tropism. It exhibits both a lytic and a latent function. The lytic cycle results in viral replication and cell death. The latent function allows for the virus to be maintained in the host for an extremely long period of time.

HSV can be modified for the delivery of nucleic acids to cells by producing a vector that exhibits only the latent function for long-term gene maintenance. HSV vectors are useful for nucleic acid delivery because they allow for a large DNA insert of up to or greater than 20 kilobases; they can be produced with extremely high titers; and they have been shown to express nucleic acids for a long period of time in the central nervous system as long as the lytic cycle does not occur.

In other particular embodiments of the present invention, the delivery vector of interest is a retrovirus. Retroviruses normally bind to a virus-specific cell surface receptor, e.g., CD4 (for HIV); CAT (for MLV-E; ecotropic Murine leukemic virus E); RAM1/GLVR2 (for murine leukemic virus-A; MLV-A); GLVR1 (for Gibbon Ape leukemia virus (GALV) and Feline leukemia virus B (FeLV-B)). The development of specialized cell lines (termed "packaging cells") which produce only replication-defective retroviruses has increased the utility of retroviruses for gene therapy, and defective retroviruses are characterized for use in gene transfer for gene therapy purposes (for a review, see Miller, (1990) *Blood* 76:271). A replication-defective retrovirus can be packaged into virions which can be used to infect a target cell through the use of a helper virus by standard techniques.

Lentiviruses may also be employed as delivery vectors. The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTRs serve to promote transcription and polyadenylation of the virion RNA's. The LTR contains all other cis-acting sequences necessary for viral replication. Lentiviruses have additional genes including vif, vpr, tat, rev, vpu, nef and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins.

Five serogroups of lentiviruses are recognized, reflecting the hosts with which they are associated (primates, sheep and goats, horses, cats, and cattle). The primate lentiviruses are distinguished by the use of CD4 protein as receptor. Some serogroups have cross-reactive gag antigens (e.g., the ovine, caprine and feline lentiviruses). Exemplary lentiviruses include but are not limited to human immunodeficiency virus (e.g., HIV 1, 2 and 3), simian immunodeficiency virus (SIV), bovine immunodeficiency virus, equine infectious anemia virus (EIAV), feline immunodeficiency virus (FIV), caprine-arthritis-encephalitis virus, ovine lentivirus, and Visna virus.

Lentivirus vectors are known in the art, see Naldini et al., (1996) *Science* 272:263–267; and Zufferey et al., (1997) *Nat. Biotech.* 15:871–875; U.S. Pat. Nos. 6,521,457; 6,428,953; 6,277,633; 6,165,782; 5,994,136; the disclosures of which are incorporated by reference herein in their entireties. Generally the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art.

Lentivirus vectors are often pseudotyped with an env protein from another virus (e.g., a retrovirus). The env preferably is an amphotropic envelope protein which allows transduction of cells of human and other species of interest. Examples of retroviral-derived env genes include, but are not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). Other env genes such as Vesicular stomatitis virus (VSV) protein G (VSV G) and the env genes from hepatitis viruses and influenza also can be used.

Lentiviral transfer vectors (Naldini et al., (1996) *Science* 272:263–267; Naldini et al., (1996) *Proc. Natl. Acad. Sci.* 93:11382–11388) have been used to infect human cells growth-arrested in vitro and to transduce neurons after direct injection into the brain of adult rats. The vector was efficient at transferring marker genes in vivo into the neurons and long term expression in the absence of detectable pathology was achieved. Animals analyzed ten months after a single injection of the vector, the longest time tested so far, showed no decrease in the average level of transgene expression and no sign of tissue pathology or immune reaction. (Blomer et al., (1997) *J. Virol.* 71:6641–6649). An improved version of the lentiviral vector in which the HIV virulence genes env, vif, vpr, vpu and nef were deleted without compromising the ability of the vector to transduce non-dividing cells have been developed. The multiply attenuated version represents a substantial improvement in the biosafety of the vector (Zufferey et al., (1997) *Nat. Biotech.* 15:871–875).

Yet another suitable vector is a poxvirus vector. These viruses are very complex, containing more than 100 proteins, although the detailed structure of the virus is presently unknown. Extracellular forms of the virus have two membranes while intracellular particles only have an inner membrane. The outer surface of the virus is made up of lipids and proteins that surround the biconcave core. Poxviruses are antigenically complex, inducing both specific and cross-reacting antibodies after infection. Poxvirus receptors are not presently known, but it is likely that there exists more than one given the tropism of poxvirus for a wide range of cells. Poxvirus gene expression is well studied due to the interest in using vaccinia virus as a vector for expression of nucleic acids.

In addition to viral transfer methods, such as those illustrated above, non-viral methods can also be employed. Many non-viral methods of nucleic acid transfer rely on normal mechanisms used by mammalian cells for the uptake and intracellular transport of macromolecules. In particular embodiments, non-viral nucleic acid delivery systems rely on endocytic pathways for the uptake of the nucleic acid molecule by the targeted cell. Exemplary nucleic acid delivery systems of this type include liposomal derived systems, poly-lysine conjugates, and artificial viral envelopes.

In particular embodiments, plasmid vectors are used in the practice of the present invention. Naked plasmids can be introduced into muscle cells by injection into the tissue. Expression can extend over many months, although the number of positive cells is typically low (Wolff et al., (1989) *Science* 247:247). Cationic lipids have been demonstrated to aid in introduction of nucleic acids into some cells in culture (Felgner and Ringold, (1989) *Nature* 337:387). Injection of cationic lipid plasmid DNA complexes into the circulation of mice has been shown to result in expression of the DNA in lung (Brigham et al., (1989) *Am. J. Med. Sci.* 298:278). One advantage of plasmid DNA is that it can be introduced into non-replicating cells.

In a representative embodiment, a nucleic acid molecule (e.g., a plasmid) can be entrapped in a lipid particle bearing positive charges on its surface and, optionally, tagged with antibodies against cell surface antigens of the target tissue (Mizuno et al., (1992) *No Shinkei Geka* 20:547; PCT publication WO 91/06309; Japanese patent application 1047381; and European patent publication EP-A-43075).

Liposomes that consist of amphiphilic cationic molecules are useful non-viral vectors for nucleic acid delivery in vitro and in vivo (reviewed in Crystal, *Science* 270: 404–410 (1995); Blaese et al., *Cancer Gene Ther.* 2: 291–297 (1995); Behr et al., *Bioconjugate Chem.* 5: 382–389 (1994); Remy et al., *Bioconjugate Chem.* 5: 647–654 (1994); and Gao et al., *Gene Therapy* 2: 710–722 (1995)). The positively charged liposomes are believed to complex with negatively charged nucleic acids via electrostatic interactions to form lipid:nucleic acid complexes. The lipid:nucleic acid complexes have several advantages as nucleic acid transfer vectors. Unlike viral vectors, the lipid:nucleic acid complexes can be used to transfer expression cassettes of essentially unlimited size. Since the complexes lack proteins, they can evoke fewer immunogenic and inflammatory responses. Moreover, they cannot replicate or recombine to form an infectious agent and have low integration frequency. A number of publications have demonstrated that amphiphilic cationic lipids can mediate nucleic acid delivery in vivo and in vitro (Felgner et al., *Proc. Natl. Acad. Sci. USA* 84: 7413–17 (1987); Loeffler et al., *Methods in Enzymology* 217: 599–618 (1993); Felgner et al., *J. Biol. Chem.* 269: 2550–2561 (1994)).

Several groups have reported the use of amphiphilic cationic lipid:nucleic acid complexes for in vivo transfection both in animals and in humans (reviewed in Gao et al., *Gene Therapy* 2: 710–722 (1995); Zhu et al., *Science* 261: 209–211 (1993); and Thierry et al., *Proc. Natl. Acad. Sci. USA* 92: 9742–9746 (1995)). U.S. Pat. No. 6,410,049 describes a method of preparing cationic lipid:nucleic acid complexes that have a prolonged shelf life.

IV. Gene Transfer Technology.

The delivery vectors of the present invention provide a means for delivering heterologous nucleic acid sequences into a broad range of cells, including dividing and non-dividing cells. The delivery vectors may be employed to transfer a nucleotide sequence of interest to a cell in vitro, e.g., to produce a polypeptide in vitro or for ex vivo gene therapy. The vectors are additionally useful in a method of delivering a nucleotide sequence to a subject in need thereof, e.g., to express an immunogenic or therapeutic polypeptide. In this manner, the polypeptide may thus be produced in vivo in the subject. The subject may be in need of the polypeptide because the subject has a deficiency of the polypeptide, or because the production of the polypeptide in the subject may impart some therapeutic effect, as a method of treatment or otherwise, and as explained further below.

In general, the vectors of the present invention may be employed to deliver any nucleic acid with a biological effect to treat or ameliorate the symptoms associated with any disorder related to gene expression. Illustrative disease states include, but are not limited to: cystic fibrosis (and other diseases of the lung), hemophilia A, hemophilia B, thalassemia, anemia and other blood disorders, AIDs, cancer (e.g., brain tumors), diabetes mellitus, muscular dystrophies (e.g., Duchenne, Becker), Gaucher's disease, Hurler's disease, adenosine deaminase deficiency, glycogen storage diseases and other metabolic defects, mucopolysaccharide disease, and diseases of solid organs (e.g., brain, liver, kidney, heart), and the like.

In particular embodiments, the delivery vectors of the invention may be administered to treat diseases of the CNS, including genetic disorders, neurodegenerative disorders, psychiatric disorders and tumors. Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease, Lesch-Nyan disease, epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The delivery vectors of the present invention can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly( e.g., in the sub-Tenon's region). One or more neurotrophic factors may also be co-delivered, either intraocularly (e.g., intravitreally) or periocularly.

Uveitis involves inflammation. One or more anti-inflammatory factors can be administered by intraocular (e.g., vitreous or anterior chamber) administration of a delivery vector of the invention.

Retinitis pigmentosa, by comparison, is characterized by retinal degeneration. In representative embodiments, retinitis pigmentosa can be treated by intraocular (e.g., vitreal) administration of a delivery vector encoding one or more neurotrophic factors.

Age-related macular degeneration involves both angiogenesis and retinal degeneration. This disorder can be treated by administering the inventive deliver vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, preferably intravitreally.

In other embodiments, the present invention may be used to treat seizures, e.g., to reduce the onset, incidence or severity of seizures. The efficacy of a therapeutic treatment for seizures can be assessed by behavioral (e.g., shaking, ticks of the eye or mouth) and/or electrographic means (most seizures have signature electrographic abnormalities). Thus, the invention can also be used to treat epilepsy, which is marked by multiple seizures over time.

In one representative embodiment, somatostatin (or an active fragment thereof) is administered to the brain using a delivery vector of the invention to treat a pituitary tumor. According to this embodiment, the delivery vector encoding somatostatin (or an active fragment thereof) is administered by microinfusion into the pituitary. Likewise, such treatment can be used to treat acromegaly (abnormal growth hormone secretion from the pituitary). The nucleic acid (e.g., Gen-Bank Accession No. J00306) and amino acid (e.g., GenBank Accession No. P01166; contains processed active peptides somatostatin-28 and somatostatin-14) sequences of somatostatins are known in the art.

Alternatively, a delivery vector may be administered that encodes any therapeutic polypeptide.

The target cell may already express an endogenous gene encoding the polypeptide being transferred by the delivery vector. The present invention may be employed to provide higher levels of expression of the polypeptide, to achieve secretion of the polypeptide, or to provide for greater regulation of polypeptide expression.

Finally, the delivery vectors produced according to the instant invention find further use in diagnostic and screening methods, whereby a gene of interest is transiently or stably expressed in a cell culture system, or alternatively, a transgenic animal model.

V. Delivery of Immunogenic Polypeptides.

As a further aspect, the delivery vectors of the present invention may be used to produce an immune response in a subject. According to this embodiment, a delivery vector comprising a nucleotide sequence encoding an immunogen may be administered to a subject, and an active immune response is mounted by the subject against the immunogen. Immunogens are as described hereinabove. Preferably, a protective immune response is elicited.

Alternatively, the delivery vector may be administered to a cell ex vivo and the altered cell is administered to the subject. The heterologous nucleotide sequence is introduced into the cell, and the cell is administered to the subject, where the heterologous nucleotide sequence encoding the immunogen is preferably expressed and induces an immune response in the subject against the immunogen. In exemplary embodiments, the cell is an antigen presenting cell (e.g., a dendritic cell) or a cancer cell.

As a further alternative, the immunogen may be presented on the surface of a virion. The use of parvoviruses (including AAV) expressing a foreign antigen(s) in the capsid for use as a vaccine is known in the art (see, e.g., Miyamura et al., (1994) *Proc. Nat. Acad. Sci USA* 91:8507; U.S. Pat. No. 5,916,563 to Young et al., U.S. Pat. No. 5,905,040 to Mazzara et al., U.S. Pat. Nos. 5,882,652, 5,863,541 to Samulski et al.; the disclosures of which are incorporated herein in their entirety by reference). Alternatively, the antigen may be expressed from a heterologous nucleic acid incorporated into a recombinant viral genome.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation,* in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment of disease, in particular cancer or tumors (e.g., by causing regression of a cancer or tumor and/or by preventing metastasis and/or by preventing growth of metastatic nodules). The protective effects may be complete or partial, as long as some benefit is conferred to the subject.

According to the foregoing methods of inducing an immune response in a subject, it is preferred that the delivery vector carrying the heterologous nucleotide sequence is administered in an immunogenically effective amount, as described below.

The delivery vectors according to the present invention may also be administered for cancer immunotherapy by administration of a vector expressing cancer cell antigens or any other immunogen that produces an immune response against a cancer cell. To illustrate, an immune response may be produced against a cancer cell antigen in a subject by administering a vector comprising a heterologous nucleotide sequence encoding the cancer cell antigen, for example to treat a patient with cancer. The delivery vector may be administered to a subject in vivo or by using ex vivo methods, as described herein.

As used herein, the term "cancer" encompasses tumor-forming cancers. Likewise, the term "cancerous tissue" encompasses tumors.

The term "cancer" has its understood meaning in the art, for example, an uncontrolled growth of tissue that has the potential to spread to distant sites of the body (i.e., metastasize). Exemplary cancers include, but are not limited to, leukemias, lymphomas, colon cancer, renal cancer, liver cancer, breast cancer, lung cancer, prostate cancer, ovarian cancer, melanoma, and the like. In embodiments of the invention, the cancer is a brain cancer or other cancer of the CNS. In particular embodiments, the invention is practiced to treat and/or prevent tumor-forming cancers (e.g., a brain tumor).

The term "tumor" is also understood in the art, for example, as an abnormal mass of undifferentiated cells within a multicellular organism. Tumors can be malignant or benign.

By the terms "treating cancer" or "treatment of cancer", it is intended that the severity of the cancer is reduced or the cancer is at least partially eliminated. In representative embodiments, these terms indicate that metastasis of the cancer is reduced or at least partially eliminated. By the terms "prevention of cancer" or "preventing cancer" it is intended that the methods at least partially eliminate or reduce the incidence or onset of cancer. Alternatively stated, the onset of cancer in the subject may be slowed, controlled, decreased in likelihood or probability, or delayed.

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the inventive delivery vectors.

Cytokines may be administered by any method known in the art. Exogenous cytokines may be administered to the subject, or alternatively, a nucleotide sequence encoding a cytokine may be delivered to the subject using a suitable vector, and the cytokine produced in vivo.

In particular embodiments, the inventive delivery vectors may be administered as part of a method of treating cancer by administering anti-cancer agents (e.g., cytokines, tumor suppressor gene products, as described above). The delivery vector may be administered to a cell in vitro or to a subject in vivo or by using ex vivo methods, as described herein and known in the art.

VI. Subjects, Pharmaceutical Formulations, and Modes of Administration.

Delivery vectors according to the present invention find use in both veterinary and medical applications. Suitable subjects include both avians and mammals, with mammals being preferred. The term "avian" as used herein includes, but is not limited to, chickens, ducks, geese, quail, turkeys and pheasants. The term "mammal" as used herein includes, but is not limited to, humans, bovines, ovines, caprines, equines, felines, canines, lagomorphs, etc. Human subjects include neonates, infants, juveniles, and adults.

In representative embodiments, administration of a delivery vector of the invention comprising a heterologous nucleic acid to a cell or subject results in expression of the heterologous nucleic acid and production of the encoded polypeptide for at least about one week, two weeks, four weeks, two months, three months, four month, six months, twelve months or longer.

In particular embodiments, the present invention provides a pharmaceutical composition comprising a delivery vector of the invention in a pharmaceutically acceptable carrier and/or other medicinal agents, pharmaceutical agents, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

By "pharmaceutically acceptable" it is meant a material that is not biologically or otherwise undesirable, i.e., the material may be administered to a subject without causing any undesirable biological effects. Thus, such a pharmaceutical composition may be used, for example, in introduction of a vector into a cell ex vivo or in administering a delivery vector or cell directly to a subject.

One aspect of the present invention is a method of transferring a nucleotide sequence to a cell in vitro. In the case of a viral delivery vector, the virus particles may be added to the cells at the appropriate multiplicity of infection according to standard transduction methods appropriate for the particular target cells. Titers of virus to administer can vary, depending upon the target cell type and number, and the particular virus vector, and may be determined by those of skill in the art without undue experimentation. Preferably, at least about $10^3$ infectious units, more preferably at least about $10^5$ infectious units, or even at least about $10^7$ infectious units, are administered to the cell.

The cell(s) to be administered the delivery vector may be of any type, including but not limited to lung cells, epithelial cells (e.g., gut and respiratory epithelial cells), muscle cells, dendritic cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. Alternatively, the cell may be any progenitor cell. As a further alternative, the cell can be a stem cell (e.g., neural stem cell, liver stem cell). As still a further alternative, the cell may be a cancer or tumor cell (e.g., brain tumor cell, including pituitary tumor cells). Moreover, the cells can be from any species of origin, as indicated above.

In particular embodiments, the cell is a cell of the central nervous system, including but not limited to: a neuron (e.g., a pyramidal, multipolar, fusiform and ganglion cell), an oligodendrocyte, an astrocyte, a microglial cell, a fibroblast, an endothelial cell, an astroglial cell, or an ependymal cell. The cells of the CNS include cells of the eye including retinal cells, retinal pigment epithelium, and corneal cells.

The delivery vectors may be administered to cells in vitro for the purpose of administering the modified cell to a subject. In particular embodiments, the cells have been removed from a subject, the delivery vector is introduced therein, and the cells are then replaced back into the subject. Methods of removing cells from subject for treatment ex vivo, followed by introduction back into the subject are known in the art (see, e.g., U.S. Pat. No. 5,399,346; the disclosure of which is incorporated herein in its entirety). Alternatively, the recombinant delivery vector is introduced into cells from another subject, into cultured cells, or into cells from any other suitable source, and the cells are administered to a subject in need thereof.

Suitable cells for ex vivo gene therapy are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$, preferably about $10^3$ to about $10^6$ cells, will be administered per dose in a pharmaceutically acceptable carrier. The cells transduced with the delivery vector are preferably administered to the subject in a therapeutically effective amount (as defined above) in combination with a pharmaceutical carrier.

In some embodiments, cells that have been transduced with a delivery vector according to the invention may be administered to elicit an immunogenic response against the delivered polypeptide (e.g., expressed as a transgene or in the capsid). Typically, a quantity of cells expressing an immunogenic amount of the polypeptide in combination with a pharmaceutically acceptable carrier is administered. An "immunogenic amount" is an amount of the expressed polypeptide that is sufficient to evoke an active immune response in the subject to which the pharmaceutical formulation is administered. Preferably, the dosage is sufficient to produce a protective immune response (as defined above). The degree of protection conferred need not be complete or permanent, as long as the benefits of administering the immunogenic polypeptide outweigh any disadvantages thereof.

A further aspect of the invention is a method of treating subjects in vivo with the inventive delivery vectors. Administration of the delivery vectors according to the present invention to a human subject or an animal in need thereof can be by any means known in the art for administering virus and non-virus vectors. In particular embodiments, the delivery vector is administered to the subject in a therapeutically effective dose in a pharmaceutically acceptable carrier. The delivery vector is administered to achieve any beneficial therapeutic effect in the subject, as described above (e.g., to treat a disease state or condition).

The delivery vectors of the invention may be administered to a subject to elicit an immunogenic response (e.g., as a vaccine). Typically, vaccines of the present invention comprise an immunogenic amount of infectious virus or non-virus vector as disclosed herein in combination with a pharmaceutically acceptable carrier. In particular embodiments, the dosage is sufficient to produce a protective immune response (as defined above). The degree of protection conferred need not be complete or permanent, as long some benefit is conferred to the subject. Immunogens are as described above.

Dosages of viral vectors to be administered to a subject will depend upon the mode of administration, the disease or condition to be treated, the individual subject's condition, the particular virus vector, and the nucleic acid to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^{13}$, $10^{14}$, $10^{15}$ transducing units or more, preferably about $10^8$–$10^{13}$ transducing units, yet more preferably $10^9$ to $10^{12}$ transducing units.

In particular embodiments, more than one administration (e.g., two, three, four or more administrations) may be employed to achieve the desired level of gene expression.

Exemplary mbdes of administration include oral, rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, intramuscular, intraventricular, intravenous, intraperitoneal, intranasal, or intraocular injections. Injectables can be prepared in conventional forms, either as liquid solutions or suspensions, solid forms suitable for solution or suspension in liquid prior to injection, or as emulsions. Alternatively, one may administer the delivery vector in a local rather than systemic manner, for example, in a depot or sustained-release formulation.

In particularly preferred embodiments of the invention, the delivery vector is administered to the CNS (e.g., to the brain or to the eye). The delivery vector may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes. cortex, basal ganglia, hippocampus and amygdala), limbic system, neocortex, corpus striatum, cerebrum, and inferior colliculus. The delivery vector may also be administered to different regions of the eye such as the retina, cornea or optic nerve.

The vector may be delivered into the cerebrospinal fluid (e.g., by lumbar puncture) for more disperse administration of the delivery vector. The vector may further be administered intravascularly to the CNS in situations in which the blood-brain barrier has been perturbed (e.g., brain tumor or cerebral infarct).

The delivery vector may be administered to the desired region(s) of the CNS by any route known in the art, including but not limited to, intrathecal, intra-ocular, intracerebral, intraventricular, intranasal, intra-aural, intra-ocular (e.g., intra-vitreous, sub-retinal, anterior chamber) and peri-ocular (e.g., sub-Tenon's region) delivery.

Typically, the delivery vector will be administered in a liquid formulation by direct injection (e.g., stereotactic injection) to the desired region or compartment in the CNS. In other embodiments, the vector may be provided by topical application to the desired region or by intra-nasal administration of an aerosol formulation. Administration to the eye or into the ear, may be by topical application of liquid droplets. As a further alternative, the delivery vector may be administered as a solid, slow-release formulation. Controlled release of parvovirus and AAV vectors is described by international patent publication WO 01/91803.

In other embodiments, a nucleotide sequence of interest is administered to the liver of the subject. Administration to the liver may be achieved by any method known in the art, including, but not limited to intravenous administration, intraportal administration, intrabiliary administration, intra-arterial administration, and direct injection into the liver parenchyma.

In other preferred embodiments, the delivery vectors are administered intramuscularly (e.g., to deliver Factor VIII or Factor IX or another protein to be secreted into the systemic circulation for delivery to target tissues), more preferably by intramuscular injection or by local administration (as defined above).

The delivery vectors disclosed herein may be administered to the lungs of a subject by any suitable means, but are preferably administered by administering an aerosol suspension of respirable particles comprised of the delivery vectors, which the subject inhales. The respirable particles may be liquid or solid. Aerosols of liquid particles comprising the delivery vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the delivery vectors may likewise be produced with any solid particulate medicament aerosol generator, by techniques known in the pharmaceutical art.

Having described the present invention, the same will be explained in greater detail in the following examples, which are included herein for illustration purposes only, and which are not intended to be limiting to the invention.

EXAMPLE 1

GFP and GAL AAV Plasmid Constructs

The fibronectin signal sequence (FIB, nucleotides 208–303, 5'-ATG CTC AGG GGT CCG GGA CCC GGG CGG CTG CTG CTG CTA GCA GTC CTG TGC CTG GGG ACA TCG GTG CGC TGC ACC GAA ACC GGG AAG AGC AAG AGG-3', SEQ ID NO:1) was derived from the rat fibronectin mRNA sequence (Genbank accession #X15906) and codes for the following peptide signal sequence:

```
                                    (SEQ ID NO:2)
Met Leu Arg Gly Pro Gly Pro Gly Arg Leu Leu Leu

Leu Ala Val Leu Cys Leu Gly Thr Ser Val Arg Cys

Thr Glu Thr Gly Lys Ser Lys Arg
```

Oligonucleotides corresponding to both strands were generated (Midland Certified reagent company, Midland, Tex.). The oligonucleotides containing the fibronectin signal sequence were:

FIbSS A: 5'-CCG GTA TGC TCA GGG GTC CGG GAC CCG GGC GGC     (SEQ ID NO:7)

TGC TGC TGC TAG CAG TCC TGT GCC TGG GGA CAT CGG

TGC GCT GCA CCG AAA CCG GGA AGA GCA AGA GG-3' and

FIbSS B: 5'-CCG GCC TCT TGC TCT TCC GGT TTT CGG TGC AGC GCA     (SEQ ID NO:8)

CCG ATG TCC CCA GGC ACA GGA CTG CTA GCA GCA GCA

GCC GCC CGG GTC CCG GAC CCC TGA GCA TA-3'.

Agel overhangs were included such that the annealed oligonucleotides could be ligated in front of GFP in EGF-PtTAk containing the complete tetracycline regulation system (designated here as pGFP, Haberman et al. (1998) *Gene Therapy* 5:1604) and TREGFP (designated here as pCMV-GFP, Haberman et al. (2000) *J. Virol.* 74:8732) linearized with Agel. This resulted in plasmids pFIB-tTAk and pFIB-GFP respectively. These constructs were also subcloned into the plasmid XX2 (Xiao et al. (1998) *J. Virol.* 72:2224) as a second source of intact AAV TRs and were used interchangeably with the original constructs.

The galanin mRNA sequence that corresponded to the active peptide (sequences for rat galanin at Accession numbers AAB20740 [peptide] and A28025 [mRNA] and for human galanin at Accession numbers AAA4187 [peptide] and M18102 [mRNA]; the disclosures of which are incorporated by reference herein in their entireties) was amplified by reverse transcriptase polymerase chain reaction (RT-PCR) from rat brain RNA using primers directed to the mature peptide sequence such that melting and reannealing of two separate PCR products resulted in 5' Agel and 3' NotI overhangs (Xiao et al. (1998) *J. Virol.* 72:2224). The 5' primer also included an additional ATG to insure the translational start of galanin in the absence of the FIB sequence and the 3' primer contained a stop codon to properly terminate translation. The sequence of the primers was as follows: 1) 5'-CCG GTA ATG GGC TGG ACC CTG AAC-3', SEQ ID NO:9 2) 5'-TA ATG GGC TGG ACC CTG AAC-3', SEQ ID NO:10 3) 5'-GC TCA TGT GAG GCC ATG CTT G-3', SEQ ID NO:11 4)5'-GGC CGC TCA TGT GAG GCC ATG CTT G-3', SEQ ID NO:12. The PCR product was ligated into the Agel-NotI sites of pGFP and pCMV-GFP replacing the GFP gene and resulting in plasmids pGAL and pCMV-GAL respectively. pFIB-GAL and PCMV-FIB-GAL were generated by adding the FIB oligonucleotide in the same manner as in the GFP constructs. All clones were sequenced to ensure accuracy.

FIG. 1 depicts the maps of the recombinant AAV constructs prepared as described above.

EXAMPLE 2

Virus Production and Purification

Recombinant AAV was produced as previously described (Haberman et al. (2002) *Mol. Ther.* 6:495, Xiao et al. (1998) *J. Virol.* 72:2224) within the UNC vector core. Briefly, HEK 293 cells were transfected with the transgene plasmid, pACG2 and XX6-80 via the calcium phosphate method. Cells were lysed by freeze thaw or deoxycholate, and cell lysates were centrifuged through a discontinuous iodixanol gradient. The virus was further purified over a Hi-trap heparin column (Amersham Pharmacia Biotech, Piscataway, N.J.), dialyzed into phosphate-buffered saline/5% sorbitol and stored at −80° C. until use. Recombinant virus titers were calculated by dot blot (Haberman et al. (1998) *Gene Therapy* 5:1604) and were as follows FIB-GAL: $2.3 \times 10^{10}$ particles/ml (AAV-FIB-GAL/tTAk, FIG. 1), GAL: $1.2 \times 10^{12}$ particles/ml (AAV-GAL-tTAk), FIB-GFP: $1 \times 10^{12}$ particles/ml (AAV-FIBtTAk, FIG. 1) as determined by dot blot.

EXAMPLE 3

Transfection and Cell Lysates

HEK 293 cells were maintained in DMEM supplemented with 10% FBS and penicillin/streptomycin. Cells were plated into 6 well plates and transfected 24 hours later using Superfect (Qiagen, Valencia, Calif.) or Lipofectamine 2000 (Invitrogen, Carlsbad, Calif.) according to manufacturers directions. Cells were transfected with plasmids containing GFP alone, FIB-GFP or mock transfected. At 24 hours, GFP positive cells were counted and found to be equivalent in GFP as compared to FIB-GFP. Mock cells showed no GFP fluorescence. The media was then removed and cells were incubated. The media was removed 24 hours post transfection, and cells were incubated in lysis buffer (50 mM Tris, pH 8.0, 150 mM NaCl, 50 mM NaF and 1% NP-40) for 30 min at 4° C. with gentle rocking. Lysates were centrifuged for 5 min and the supernatant was removed to a fresh tube. Both media and cell lysates were stored at −80° C. until use. To obtain extracts for the galanin ELISA, plasmids were transfected into HEK 293 cells as before. However, at 24 hours post-transfection, the media was replaced with Opti-MEM (Invitrogen), and the cells were incubated an additional 24 hours before removal and cell lysis. Cell lysis buffer and media were supplemented with leupeptin and aprotinin to inhibit peptide degradation. Both media and cell lysates were stored at −80° C. until use.

EXAMPLE 4

Western Blots

The ability of the FIB sequence to secrete gene product was determined by western blot using 5 or 20 μl of media from pGFP, pFIB-GFP and mock transfected cells. Samples were loaded onto 10% Nupage bis-tris gels in MES buffer according to the manufacturer's protocol. Gels were transferred to 0.2 μM Nitrocellulose (Invitrogen, Carlsbad, Calif.) in a Nupage wet transfer apparatus (Invitrogen) and then blocked for one hour in 10% non-fat dry milk in tris-buffered saline/0.1% tween 20 (TBS/tween). They were then incubated overnight at 4° C. in 1% non-fat dry milk in TBS/tween with 1:100 dilution of rabbit anti-GFP antibody (Research Diagnostics, Inc., Flanders, N.J.). Blots were washed in 1% non-fat dry milk in TBS/tween and incubated for 1 hour in an HRP-conjugated anti-rabbit secondary antibody (Amersham Pharmacia Biotech). Blots were developed using Supersignal chemiluminescence substrate (Pierce, Rockford, Ill.) and exposed to film. Western blots were also performed on media and cell lysates from cells transfected with pGAL, pFIB-GAL, and pFIB-GFP and mock transfected cells and probed with an anti-galanin primary antibody (Peninsula Labs, San Carlos, Calif.) followed by HRP-conjugated anti-rabbit secondary antibody. A specific anti-galanin reactive band was detected in the media and cell lysate of the pFIB-GAL media, but not the pGAL, pFIB-GFP or mock lanes (data not shown).

EXAMPLE 5

Galanin ELISA

Media from cells transfected with pGAL, and pFIB-GAL, and mock transfected cells were assessed using a galanin ELISA kit (Peninsula Labs, San Carlos, Calif.) according to manufacturers directions. Because of a low level of background reactivity in the mock transfected media, standards were assessed diluted in both buffer and in media from mock transfected cells. Results from duplicate wells were averaged and gave 0.32 ng/ml for pFIB-GAL and 0.02 ng/ml for the pGAL media. Very similar results were obtained from two separate experiments as well as when calculated from standards diluted in buffer or in mock media. Media from plasmid transfections were used for these experiments instead of virus infections due to the long latency of onset of gene expression from the tetracycline regulated virus. The long latency of onset is due a combination of the need for viral second strand synthesis before gene expression and the slow onset of the feed-forward activation of transgene expression in the regulated AAV vector construct (Haberman et al. (1998) *Gene Therapy* 5:1604).

EXAMPLE 6

Recombinant AAV Infusion and Inferior Collicular Electrode Implantation

All of the animals were pathogen-free male Sprague-Dawley rats obtained from Harlan (Indianapolis, Ind.). The animals were maintained in a 12 hour light-dark cycle and had free access to water and food. All care and procedures were in accordance with the Guide for the Care and Use of Laboratory Animals (DHHS Publication No. [NIH]85-23), and all procedures received prior approval by the University of North Carolina Institutional Animal Care and Usage Committee.

For virus vector infusions and electrode implants, animals first were anesthetized with 50 mg/kg pentobarbital and placed into a stereotaxic frame. Using a 32 gauge stainless steel injector and a Sage infusion pump, animals received 1 µl of AAV-FIB-GAL (N=6) (AAV-FIB-GAL/tTAk, FIG. 1), AAV-GAL (N=5) or AAV-FIB-GFP (N=5) (AAV-FIBtTAk, FIG. 1) over 9 minutes into the seizure sensitive site of the inferior collicular cortex (McCown et al. (1984) *Exp. Neurology* 86:527, McCown et al. (1991) *Brain Res.* 567:25) (IAL 0.2 mm, lateral 1.6 mm, vertical 3.5 mm, according to the atlas of Paxinos and Watson (Paxinos & Watson (1988) *The Rat Brain in Stereotaxic Coordinates.* Academic Press). The injector was left in place for 2 minutes post-infusion to allow diffusion from the injector. After removal of the injector, a tripolar, stimulating electrode (0.007" platinum-iridium, insulated except for the tip cross section, 400 µm vertical tip separation) was implanted into the site of AAV vector infusion, and the electrode was secured to three screws in the skull with cranioplastic cement. The animals were allowed at least 4 days to recover from the surgery before any seizure threshold tests were conducted. In a separate group (N=4), an AAV-FIB-GAL vector was infused where FIB-GAL gene expression was driven by a cytomegalovirus promoter instead of the regulated doxycycline off promoter.

For the kainic acid experiment, 2 µl of AAV-FIB-GAL (N=6) or AAV-GAL (N=5) was infused into the hilar region of the rat hippocampus (IAL 5.4 mm, lateral 2.2 mm, vertical 3.6 mm). As before, the injector was left in place for 2 minutes post-infusion to allow diffusion from the injector. No testing was conducted for 2 weeks post-infusion in order to allow adequate gene expression prior to kainic acid treatment.

EXAMPLE 7

Seizure Threshold Testing Procedure

The baseline seizure stimulation threshold current and wild running duration were determined 4 and 7 days after surgery, as previously described (McCown et al. (1984) *Exp. Neurology* 86:527). Briefly, animals were connected to a Grass Model SD9 stimulator and stimulation (30 Hz, 1.5 msec duration, monophasic square wave) was initiated at 80 µA (all stimulation currents were continuously monitored on an oscilloscope by measuring the voltage drop across a 10K ohm resistor). The stimulation current was increased 20 µA every 5 sec until the first appearance of wild running behavior. At this instance, the stimulation was terminated, and the post-stimulus wild running duration was timed. Following these first two seizure threshold determinations, the animals were tested once every seven days for 10 weeks in order to evaluate the effects of the gene transfer and expression on seizure threshold. After the seizure test on week 4, the animals received doxycycline in the drinking water (300 µg/ml), which has been shown to suppress vector derived gene expression (Haberman et al. (1998) *Gene Therapy* 5:1604). The doxycycline administration was discontinued after the seizure test on week 6. Under control, unperturbed conditions, the seizure threshold remains stable over an extended period of repeated testing (McCown et al. (1984) *Exp. Neurology* 86:527).

EXAMPLE 8

Kainic Acid Administration

For acute kainic acid treatment, animals received a 10 mg/kg i.p. dose of kainic acid (Sigma) two weeks after virus vector infusion. Using the limbic seizure scale of Racine (Racine. (1972) *Electroencephalogr. Clin. Neurophysiol.* 32:281), the latency to class I, III, IV and V limbic seizures was recorded. After 1 hour of status epilepticus, the animals received a 30 mg/kg dose of pentobarbital to terminate the seizures.

EXAMPLE 9

RT-PCR Procedure

As previously described for single acutely dissociated neurons (Criswell et al. (1998) *Neuropharmacology* 36:1641), RNA was extracted from hippocampal or inferior collicular tissue samples both on the vector infused side and the contralateral, uninfused side. The extracted RNA was reverse transcribed using poly T primers. Then the cDNA was subjected to PCR using primers specific to the FIB sequence (5'-TGC TAG CAG TCC TGT GCC TG-3', SEQ ID NO:20) and the GAL sequence (5'-ATG TGA GGC CAT GCT TGT CG-3', SEQ ID NO:21) resulting in a 163 base pair product. After 25 PCR cycles, the product was separated on an agarose gel containing ethidium bromide, illuminated on a UV light box and photographed, using a digital camera. As controls for DNA contamination, the extracted RNA was either treated with DNase before the reverse transcription or amplified with PCR without prior reverse transcription. Both cases indicated the lack of contaminating vector DNA.

EXAMPLE 10

Secretion of GFP with Fibronectin Signal Sequences

Figure 2:
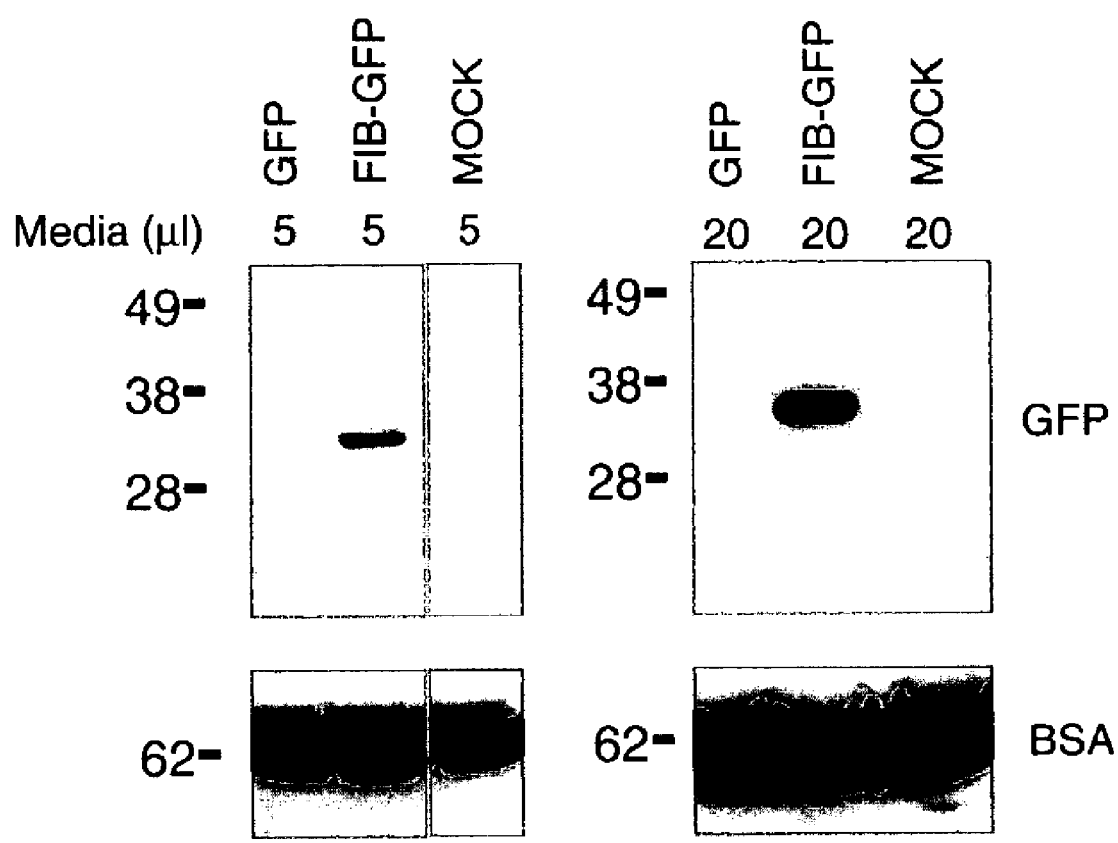
FIG. 2—Western blot of GFP in the media of FIB-GFP transfected cells. 24 hours after transfection with GFP, FIB-GFP plasmids or mock transfection, the media was removed from the cells and either 5 or 20 μl of media was analyzed by western blot with an anti-GFP antibody. The FIB-GFP transfected cells secreted significant amounts of GFP whereas the GFP transfected cells had no detectable GFP in the media with either 5 or 20 μl of media. Probing the same blot with an anti-BSA antibody demonstrated equal loading and transfer of protein in each lane.

Initially, we generated an AAV vector plasmid where the fibronectin secretory signal sequence (FIB, Schwarzbauer et al. (1987) *EMBO J.* 6, 2573) was fused to the green fluorescent protein (GFP) gene (AAV-FIB-GFP). Transfection of HeLa cells with an AAV vector plasmid containing only the GFP gene produced uniform GFP distribution across the cells with no evidence of extracellular presence. In contrast, transfection of HeLa cells with a FIB-GFP AAV vector plasmid produced a dramatically different pattern of GFP expression (data not shown). The cells appeared hollow and the media exhibited a high GFP background. Next, recombinant AAV-FIB-GFP virus was made, and neurons were transduced in the hippocampus or inferior colliculus. Normally, AAV-mediated transduction and expression of GFP in the brain produces a uniform GFP intensity across the extent of the cell body. In marked contrast, AAV-FIB-GFP transduction produced a non-uniform GFP pattern in many of the neurons, causing the neuronal cell body to appear hollow, similar to the in vitro findings (data not shown). As seen in FIG. 2, substantial GFP was present in the media of cells transfected with the FIB-GFP sequence, whereas without the FIB sequence, no GFP was found in the media. Thus, inclusion of the FIB caused gene product secretion after AAV transfection in vitro, and produced a qualitatively similar result after transduction in vivo. The fibronectin signal sequence was used to conduct further experiments with the neuropeptides galanin (gal) and neuropeptide Y (NPY) proteins (described below).

EXAMPLE 11

In Vitro Secretion of Galanin

Although it appeared that the FIB was capable of secreting an AAV-derived gene product, it remained to be demonstrated that a neuroactive peptide could be expressed and secreted in amounts necessary for physiological action. Galanin is an endogenous neuroactive peptide that is widely distributed in the CNS and modulates a number of physiological processes, including feeding behaviors and memory function (Mazarati et al. (1998) *J. Neurosci.* 18:10070, Crawley (1996) *Life Sci.* 58:2185). In addition, it has been shown that intrahippocampal infusion of galanin blocked self-sustaining hippocampal status epilepticus (Mazarati et al. (1998) *J. Neurosci.* 18:10070). Therefore, the coding sequence for the mature galanin peptide was cloned into a doxycycline off, regulatable AAV vector (Haberman et al. (1998) *Gene Therapy* 5:1604), in one case preceded by the FIB (AAV-FIB-GAL) and in the other case in the absence of the FIB (AAV-GAL). Thus, AAV-FIB-GAL vector transduction should both express and secrete galanin, while AAV-GAL vector transduction should express galanin within the cell. As an initial test of these constructs, we transfected HEK293 cells with either FIB-GAL or GAL plasmids. Twenty-four hours later the media was collected, and the presence of galanin was determined by ELISA. Neither the mock transfected nor the GAL transfected cells exhibited detectable galanin in the media, but for the FIB-GAL transfection significant galanin (32 ng /ml) was detected in the media. Given an approximate 50% transduction efficiency, it is estimated that 256 ng of galanin was secreted by $2.5 \times 10^6$ transfected cells/24 hours. As with GFP, the FIB sequence in conjunction with GAL apparently caused the secretion of galanin in vitro. Western blots of both the FIB-GFP and FIB-GAL also revealed that significant amounts of protein remained inside the cell (data not shown). Simply adding a fibronectin signal sequence was sufficient to generate secretion.

EXAMPLE 12

Modulation of Focal Seizure Activity by AAV-FIB-GAL

Figure 3:
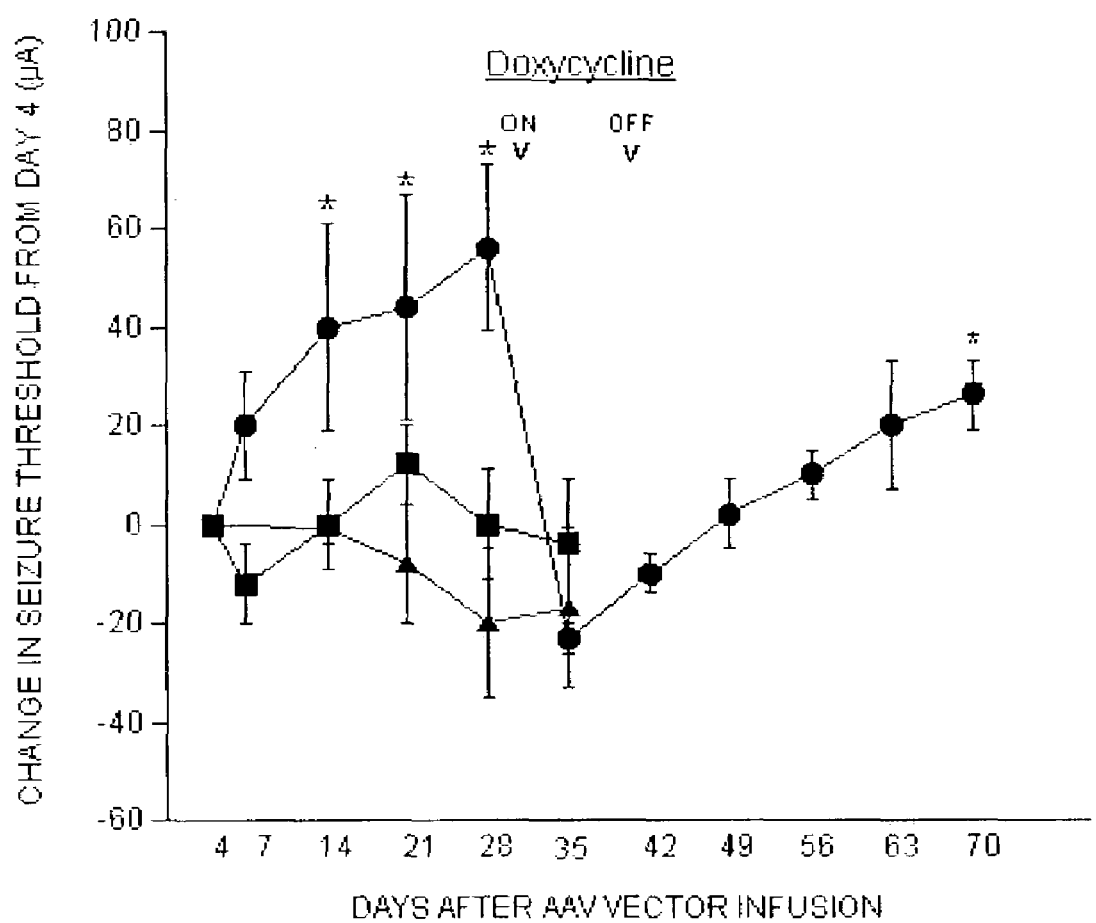
FIG. 3—The effects of AAV vector microinjections on the focal seizure sensitivity in the inferior collicular cortex. After AAV-FIB GAL vector infusion (•) the amount of stimulation current increased significantly over a 4 week period (*P<0.05, paired t-test). The oral administration of doxycycline caused a return to baseline, and upon removal of the doxycycline, the seizure threshold slowly increased. In contrast, infusion of either an AAV-GAL vector (■) or an AAV-FIB-GFP vector (▲) had no significant effect on seizure threshold.

In order to test these constructs in vivo, we first utilized a model of focal seizure genesis in the inferior collicular cortex. In this focal seizure model, brief electrical stimulation of a specific region in the inferior collicular cortex causes brief post-stimulus wild running seizure activity where the seizure behaviors exactly coincide with localized after discharge (McCown et al. (1984) *Exp. Neurology* 86:527, McCown et al. (1991) *Brain Res.* 567:25). An important property of this model is that in the absence of any perturbation, the electrical stimulation threshold for seizure genesis remains stable for long periods of time. Furthermore, the inferior colliculus supports high levels of long-term AAV-mediated gene expression that can be regulated exogenously (McCown et al. (1996) *Brain Res.* 713:99, Baron & Bujard (2000) *Methods Enzymol.* 327:401), and galanin-1 receptors are present in this brain structure (Burazin et al. (2000) *Eur. J. Neurosci.* 12:2901). After production of recombinant AAV-FIB-GAL virus, 1 μl was infused into the inferior colliculus, and a stimulating electrode was implanted. The seizure threshold was determined on post-treatment day 4 for each animal, and subsequently, the seizure genesis threshold was determined once a week. As seen in FIG. 3, over a 4 week testing period the stimulation threshold for seizure genesis increased significantly in the AAV-FIB-GAL treated group. When doxycycline was added to the drinking water following the week 4 test, within one week, the threshold for seizure genesis returned to baseline levels. Upon removal of the doxycycline, the seizure suppressive effects slowly increased, in a manner similar to the kinetics of the tetracycline-off regulation system (Baron & Bujard (2000) *Methods Enzymol.* 327:401). These changes in local seizure sensitivity most likely accrue from the secreted FIB-GAL. Transduction with an AAV-GAL vector without the FIB sequence did not significantly alter the seizure genesis threshold (see FIG. 3). Similarly, the seizure attenuation was not due to the mere secretion of a protein or the FIB sequence, because collicular transduction with an AAV-FIB-GFP vector did not significantly alter the seizure genesis threshold (see FIG. 3). Finally, this approach to seizure suppression was not influenced by a change in promoter. Collicular infusion of an AAV-FIB-GAL vector, where gene expression was driven by a CMV promoter, caused a significant elevation in the seizure threshold two weeks post-treatment (50±10 μamps; n=4; P<0.05, paired t-test).

EXAMPLE 13

Prevention of Kainic Acid-induced Hippocampal Cell Death by AAV-FIB-GAL

A well characterized animal model of temporal lobe epilepsy involves the peripheral administration of kainic acid which causes limbic seizure activity and subsequent neuronal death, especially in the hilus of the hippocampus (Nadler & Kainic (1981) *Life Sci.* 29:2031, Buckmaster & Dudek (1997) *J. Comp. Neurol.* 385:385). Because AAV vectors can transduce hilar neurons (McCown et al. (1996) *Brain Res.* 713:99) and local infusion of galanin can attenuate electrically elicited hippocampal seizure activity (Mazarati et al. (1998) *J. Neurosci.* 18:10070), attenuation of local seizure activity by AAV-FIB-GAL should protect nearby neurons from kainic acid-induced cell death. Therefore, we unilaterally infused the AAV-FIB-GAL vectors (2 μl) into the hilar region of the hippocampus. Two weeks later, the animals were treated with 10 mg/kg kainic acid, i.p., and the appearance of limbic seizure behaviors was determined. The infusion of AAV-FIB-GAL did not alter the time to onset or severity of the limbic seizure behaviors compared to uninfused controls. This result was expected, because only a small unilateral region of the hippocampus was transduced.

EXAMPLE 14

Transferrin AAV Plasmid Constructs

Vector constructs containing the transferrin signal sequence were prepared in a similar manner to those containing the fibronectin signal sequences. Because the transferrin 5'-untranslated region was very short, the entire 5'-untranslated mRNA sequence plus the signal sequence was included. The signal sequence for transferrin was encoded by underlined nucleotides 18–74 of the 5' transferrin sequence of Accession No. NM_017055:

```
                                           (SEQ ID NO:13)
5'-CCACACACACCGAGAGG ATG AGG TTC GCT GTG GGT GCC

CTG CTG GCT TGT GCC GCC CTG GGA CTG TGT CTG GCT-3'
``` and codes for the following peptide signal sequence:

```
                                           SEQ ID NO:17)
Met Arg Phe Ala Val Gly Ala Leu Leu Ala Cys Ala Ala

Leu Gly Leu Cys Leu Ala;
```

Oligonucleotides containing the transferrin signal sequence were:

```
TrfSS A  5'-CCG GTC CAC ACA CAC CGA GAG GAT GAG GTT CGC TGT  (SEQ ID NO:18)
            GGG TGC CCT GCT GGC TTG TGC CGC CCT GGG ACT GTG
            TCT GGC T-3' and TrfSS B  5'-CCG GAG CCA GAC ACA GTC CCA GGG CGG CAC AAG CCA  (SEQ ID NO:19)
            GCA GGG CAC CCA CAG CGA ACC TCA TCC TCT CGG TGT
            GTG TGG A-3'.
```

Figure 4:
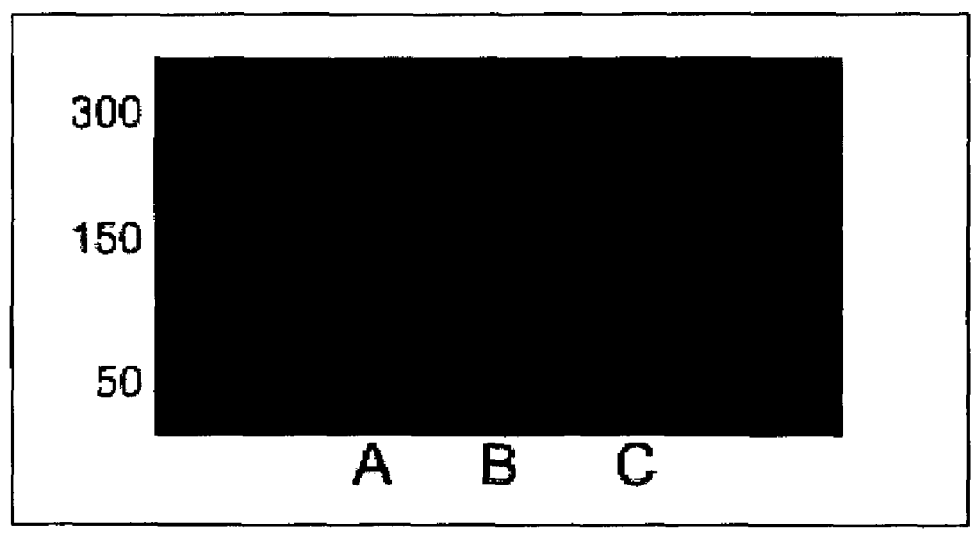
FIG. 4—RT-PCR of RNA extracted from hippocampal tissue either on the AAV-FIB-GAL infused side (A) or the contralateral uninjected side (B) 4 months after vector infusion. The primers were designed to recognize the FIB-GAL cDNA, producing a PCR product of 163 base pairs. Note the correct product in lane A, but the absence of product in lane B. DNAse treatment (C) or omission of the RT (D) resulted in no product after the PCR, indicating the absence of contaminating viral DNA.

However, two weeks post-kainic acid, histological evaluation of the brains show that an area around the AAV-FIB-GAL infusion was spared the classic cell death found on the contralateral, untreated side (number of neurons in the untreated hilar region equaled 35±12% of the neurons present in the AAV-FIB-GAL treated hilar region, n=5, P<0.05, paired t-test, data not shown). Furthermore, the AAV-FIB-GAL side appeared no different from the normal untreated hippocampus, whereas unilateral infusion of AAV-GAL vectors did not protect the hilar neurons from kainic acid-induced cell death, exhibiting no significant difference between the infused and uninfused sides (number of hilar neurons in the untreated hilar region equaled 107±15% of the AAV- GAL treated hippocampus, n=6, P>0.1, data not shown). In a separate group of rats (n=4), RT-PCR of hippocampal tissue showed that the appropriate mRNA was being produced (see FIG. 4, lane A) one month after unilateral infusion of the AAV-FIB-GAL (2 μl). The contralateral hippocampus did not contain any FIB-GAL mRNA (FIG. 4, lane B) and omission of the RT step indicates that no contaminating DNA was present (FIG. 4, lane C). Similar results have been obtained 4 months after hippocampal transfection. Thus, it appears that AAV-FIB-GAL transduction produces the appropriate mRNA for long periods of time in vivo.

GFP fused to the transferrin signal sequence (TRANS-GFP) and vectors containing TRANS-GFP were prepared in the same manner as FIB-GFP described in Example 1, substituting the transferrin signal sequence oligonucleotides (SEQ ID NOS:18 and 19) for the fibronectin signal sequence oligonucleotides previously described (SEQ ID NOS:7 and 8).

EXAMPLE 15

Localization of GFP with Transferrin Signal Sequences

Transfection of HeLa cells with the AAV-TRANS-GFP plasmid DNA and transduction of neurons in the hippocampus or inferior colliculus with recombinant AAV-TRANS-GFP virus were performed in the same manner as described in Example 10 with the fibronectin constructs. In both cases, TRANS-GFP produced a uniform pattern of fluorescence similar to wild-type GFP (data not shown).

EXAMPLE 16

Suppression of Seizure Sensitivity by AAV-FIB-NPY/tTAk

AAV vectors containing DNA encoding the neuroactive peptide neuropeptide Y (NPY) preceded by the fibronectin secretory sequence were generated and infused into rat brain, and the effects on NPY administration on seizure genesis threshold evaluated.

The sequences of human and rat NPY are the same. The human NPY nucleotide sequence (GenBank accession number M15789) and peptide sequence (GenBank accession number AAA59946) are incorporated herein by reference in their entireties. NPY affects various brain functions, and can suppress seizures. An AAV-FIB-NPY/tTAk (FIG. 1) vector was produced in the same manner as the AAV-FIB-GAL vectors (described above).

Figure 5:
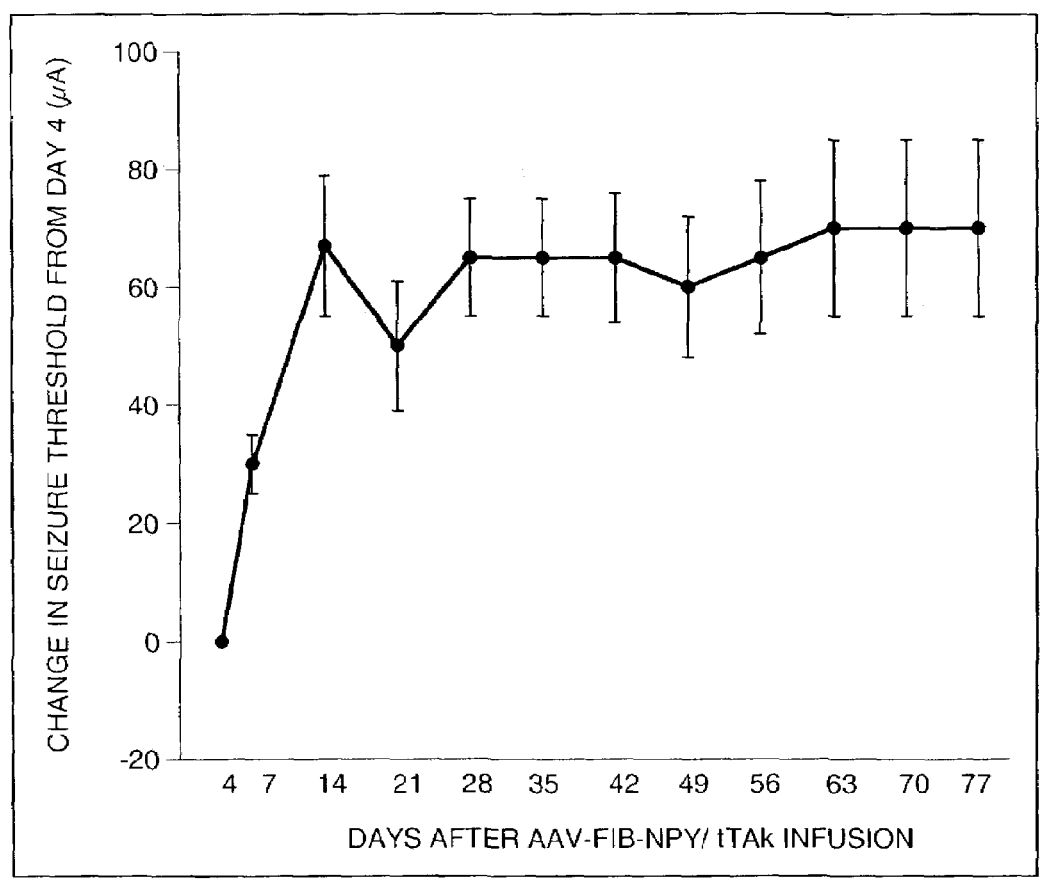
FIG. 5—Suppression of seizure sensitivity by AAV-FIB-NPY viral vectors. Rats received microinfusions of AAV viral vectors containing the DNA coding sequence for the neuroactive peptide, Neuropeptide Y, preceded by the fibronectin secretory sequence (FIB). Immediately following the infusion into a seizure sensitive brain site, a stimulating electrode was implanted. Four days after the surgery, the electrical stimulation threshold for seizure genesis was determined. Subsequently, the seizure genesis threshold was determined on post-surgery day 7 and once a week thereafter.

Rats received microinfusions of the AAV-FIB-NPY vectors containing DNA encoding NPY preceded by the fibronectin secretory sequence (FIB). Immediately following the infusion into a seizure sensitive brain site, the inferior colliculus, a stimulating electrode was implanted. Four days after the surgery, the electrical stimulation threshold for seizure genesis was determined. Subsequently, the seizure genesis threshold was determined on post-surgery day 7 and once a week thereafter. Normally, this seizure genesis threshold does not change over time. However, as shown in FIG. 5, it can be seen that microinjection of the AAV vector caused a significant elevation of the seizure threshold for over 3 months. Thus, the expression and FIB mediated secretion of the NPY suppressed seizure activity in the brain.

The invention is described by the following claims, with equivalents of the claims to be included therein.

What is claimed is:

1. A delivery vector comprising:
a) an adenovirus associated (AAV) vector genome comprising 5' and 3' AAV inverted terminal repeat (ITR) sequences;
b) a first nucleotide sequence encoding a polypeptide of interest; and
c) a second nucleotide sequence encoding a fibronectin secretory signal sequence that is operatively associated with the first nucleotide sequence of (b), wherein the second nucleotide sequence is selected from the group consisting of:

(i) the nucleotide sequence of SEQ ID NO:1, SEQ ID NO:14 or SEQ ID NO:15;
(ii) a nucleotide sequence encoding the amino acid sequence of SEQ ID NO:2 or an active fragment thereof having secretory signal activity, SEQ ID NO:5 or an active fragment thereof having secretory signal activity, or SEQ ID NO:6 or an active fragment thereof having secretory signal activity; and
a nucleotide sequence that differs from the nucleotide sequence of (ii) above due to the degeneracy of the genetic code, and wherein the second nucleotide sequence does not contain nucleic acids that encode fibronectin amino acid sequence beyond the carboxy terminal side of the cleavage site of the signal sequence.

2. A pharmaceutical composition comprising the delivery vector of claim 1 in a pharmaceutically acceptable carrier.

3. The delivery vector of claim 1, wherein said AAV vector genome does not encode AAV Rep or AAV capsid proteins.

4. The delivery vector of claim 1, wherein said first nucleotide sequence encoding a polypeptide of interest is operatively associated with an inducible promoter.

5. The delivery vector of claim 4, wherein said inducible promoter is selected from the group consisting of a dexamethasone inducible promoter, a tetracycline regulated promoter, an RU486-inducible promoter, an endysone-inducible promoter, a rapamycin-inducible promoter, and a metallothionein promoter.

6. The delivery vector of claim 1, wherein said first nucleotide sequence encoding a polypeptide of interest is operatively associated with a promoter that is functional in the central nervous system.

7. The delivery vector of claim 1, wherein said polypeptide of interest is galanin.

8. The delivery vector of claim 1, wherein said polypeptide of interest is selected from the group consisting of galanin, neuropeptide Y, cholecystokinin, thyrotropin-releasing hormone, neurotensin, oxytocin, acidic fibroblast growth factor, basic fibroblast growth factor, glial cell derived growth factor, met-enkephalin, leu-enkephalin, dynorphin, β-endorphin, leptin, a semaphorin peptide, tyrosine hydroxylase, aromatic amino acid decarboxylase, brain-derived neurotrophic factor, nerve growth factor, superoxide dismutase, catalase, glutathione peroxidase, adenosine A-1 receptor, GABA-A receptor, glutamate decarboxylase, neurotrophic factor-3, neurotrophic factor-4 and somatostatin.

9. A method of delivering a nucleic acid to a cell of the central nervous system, comprising contacting the cell with the delivery vector of claim 1 under conditions sufficient for the delivery vector to be introduced into the cell.

10. The method of claim 9, wherein the cell is selected from the group consisting of:
(a) a brain cell;
b) a neuron, astrocyte, oligodendrocyte, microglial cell, fibroblast, endothelial cell, astroglial cell, or ependymal cell; and
(c) a cell from the limbic system, spinal cord, neocortex, thalamus, hypothalamus, epithalamus, pineal gland, corpus striatum, cerebrum, basal ganglia, amygdala, brainstem, cerebrum, cerebellum, striatum, hippocampus, inferior colliculus, pituitary or substantia nigra.

11. The method of claim 9 wherein the delivery vector is formulated in a pharmaceutically acceptable carrier.

12. The method of claim 11, wherein the subject has epilepsy.

13. The method of claim 11, wherein said administering step is carried out by direct injection.

14. The method of claim 11, wherein said administering step is carried out by stereotaxic injection.

15. The method of claim 11, wherein said administering step is to a region of the brain.

16. The method of claim 11, wherein said administering step is to a region selected from the group consisting of the limbic system, spinal cord, neocortex, thalamus, hypothalamus, epithalamus, pineal gland, corpus striatum, cerebrum, basal ganglia, amygdala, brainstem, cerebrum, cerebellum, striatum, hippocampus, pituitary gland and substantia nigra.

* * * * *

UNITED STATES PATENT AND TRADEMARK OFFICE
CERTIFICATE OF CORRECTION

| | | |
|---|---|---|
| PATENT NO. | : 7,071,172 B2 | Page 1 of 1 |
| APPLICATION NO. | : 10/425328 | |
| DATED | : July 4, 2006 | |
| INVENTOR(S) | : McCown et al. | |

It is certified that error appears in the above-identified patent and that said Letters Patent is hereby corrected as shown below:

Column 56,
Line 2 should read -- central nervous system (CNS), comprising administering directly to a CNS region or compartment proximal to said cell --

Signed and Sealed this

Twenty-first Day of November, 2006

JON W. DUDAS
*Director of the United States Patent and Trademark Office*